United States Patent
Hickman et al.

(10) Patent No.: US 9,650,606 B2
(45) Date of Patent: *May 16, 2017

(54) METHOD OF CO-CULTURING MAMMALIAN MUSCLE CELLS AND MOTONEURONS

(71) Applicant: UNIVERSITY OF CENTRAL FLORIDA RESEARCH FOUNDATION, INC., Orlando, FL (US)

(72) Inventors: James Hickman, Orlando, FL (US); Mainak Das, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 228 days.

This patent is subject to a terminal disclaimer.

(21) Appl. No.: 14/299,802

(22) Filed: Jun. 9, 2014

(65) Prior Publication Data

US 2014/0302599 A1    Oct. 9, 2014

Related U.S. Application Data

(63) Continuation of application No. 12/765,996, filed on Apr. 23, 2010, now Pat. No. 8,815,584.

(60) Provisional application No. 61/171,958, filed on Apr. 23, 2009.

(51) Int. Cl.
   *C12N 5/0793*   (2010.01)
   *C12N 5/077*    (2010.01)

(52) U.S. Cl.
   CPC .......... *C12N 5/0619* (2013.01); *C12N 5/0658* (2013.01); *C12N 2500/90* (2013.01); *C12N 2502/088* (2013.01); *C12N 2502/1335* (2013.01)

(58) Field of Classification Search
   None
   See application file for complete search history.

(56) References Cited

U.S. PATENT DOCUMENTS

| | | |
|---|---|---|
| 5,442,510 A | 8/1995 | Schwartz |
| 5,682,899 A | 11/1997 | Nashef |
| 5,948,621 A | 9/1999 | Turner |
| 6,866,383 B2 | 3/2005 | Naik |
| 6,916,541 B2 | 7/2005 | Pantano |
| 6,935,165 B2 | 8/2005 | Bashir |
| 7,384,786 B2 | 6/2008 | Freyman |
| 7,541,146 B2 | 6/2009 | Lewis |
| 7,579,189 B2 | 8/2009 | Freyman |
| 7,691,629 B2 | 4/2010 | Johe |
| 7,860,563 B2 | 12/2010 | Foreman |
| 7,923,015 B2 | 4/2011 | Vazquez-Martinez |
| 7,927,671 B2 | 4/2011 | Kato |
| 8,071,319 B2 | 12/2011 | Metzger |
| 8,178,602 B2 | 5/2012 | Mao |
| 8,318,488 B1 | 11/2012 | Bohlen |
| 8,318,489 B2 | 11/2012 | Davidson |
| 8,318,951 B2 | 11/2012 | Olson |
| 2003/0065452 A1 | 4/2003 | Hickman |
| 2003/0144823 A1 | 7/2003 | Fox |
| 2003/0211542 A1 | 11/2003 | Lee |
| 2006/0105457 A1 | 5/2006 | Rameshwar |
| 2006/0259992 A1 | 11/2006 | Koren |
| 2007/0015138 A1 | 1/2007 | Barlow |
| 2007/0117217 A1 | 5/2007 | Lal |
| 2007/0129447 A1 | 6/2007 | Sra |
| 2007/0212723 A1 | 9/2007 | Dudley |
| 2008/0124789 A1 | 5/2008 | Hickman |
| 2008/0227137 A1 | 9/2008 | Zhang |
| 2009/0029463 A1 | 1/2009 | Collins |
| 2009/0227469 A1 | 9/2009 | Conklin |
| 2009/0239940 A1 | 9/2009 | Del Monte |

(Continued)

FOREIGN PATENT DOCUMENTS

| | | |
|---|---|---|
| CA | 2788905 | 2/2011 |
| CA | 2798777 | 5/2011 |

(Continued)

OTHER PUBLICATIONS

Brewer et al. "NbActiv4 medium improvement to Neurobasal/B27 increases neuron synapse densities and network spike rates on multielectrode arrays" J Neurosci Methods, 2008, 170:181-187.*
Bergener and Butler (2005). "Chapter 3 Medium Development" In S.S. Ozturk and W-S. Hu (Eds) Cell Culture Technology for Pharmaceutical and Cell-Based Therapies (pp. 41 and 60-62). Boca Raton, FL: Taylor & Francis Group.*
Freshney, Ian. (2000). Culture of Animal Cells: A manual of basic technique. (4th ed). New York: Wiley-Liss. pp. 100.*
Abbanat D, et al. (2003) Novel antibacterial agents for the treatment of serious Gram-positive infections. Expert Opin Investig Drugs. 12: 379-399.

(Continued)

*Primary Examiner* — Allison Fox
(74) *Attorney, Agent, or Firm* — Meunier Carlin & Curfman LLC

(57) ABSTRACT

The invention provides a method of co-culturing mammalian muscle cells and mammalian motoneurons. The method comprises preparing one or more carriers coated with a covalently bonded monolayer of trimethoxysilylpropyl diethylenetriamine (DETA); suspending isolated fetal mammalian skeletal muscle cells in serum-free medium according to medium composition 1; suspending isolated fetal mammalian spinal motoneurons in serum-free medium according to medium composition 1; plating the suspended muscle cells onto the one or more carriers at a predetermined density and allowing the muscle cells to attach; plating the suspended motoneurons at a predetermined density onto the one or more carriers and allowing the motoneurons to attach; covering the one or more carriers with a mixture of medium composition 1 and medium composition 2; and incubating the carriers covered in the media mixture.

7 Claims, 4 Drawing Sheets

(56) References Cited

U.S. PATENT DOCUMENTS

| | | |
|---|---|---|
| 2009/0305319 A1 | 12/2009 | Baudenbacher |
| 2012/0128639 A1 | 5/2012 | Hickman |
| 2014/0206028 A1 | 7/2014 | Hickman |

FOREIGN PATENT DOCUMENTS

| | | |
|---|---|---|
| EP | 2434896 | 4/2012 |
| EP | 2435585 | 4/2012 |
| EP | 2531910 | 12/2012 |
| EP | 2585171 | 5/2013 |
| WO | 01/29206 | 4/2001 |
| WO | 2005/033264 | 4/2005 |
| WO | 2007/044314 | 4/2007 |
| WO | 2010/127280 | 11/2010 |
| WO | 2010/138679 | 12/2010 |
| WO | 2010/138782 | 12/2010 |
| WO | 2011/097574 | 8/2011 |
| WO | 2011/133985 | 10/2011 |
| WO | 2012/158923 | 11/2012 |
| WO | 2013/013206 | 1/2013 |
| WO | 2014/028940 | 2/2014 |

OTHER PUBLICATIONS

Abdi H. (2003) Multivariate Analysis. Encyclopedia of Social Sciences Research Methods. M. Lewis-Beck, A. Bryman and T. Futing. Thousand Oaks (CA), Sage.
Adell A, et al. (2002) Origin and functional role of the extracellular serotonin in the midbrain raphe nuclei. Brain Res Brain Res Rev. 39: 154-180.
Agarwal A, et al. (2013) Microfluidic heart on a chip for higher throughput pharmacological studies. Lab Chip. 13: 3599-3608.
Ahern CA, et al. (2003) Ca2+ current and charge movements in skeletal myotubes promoted by the beta-subunit of the dihydropyridine receptor in the absence of ryanodine receptor type 1. Biophys J. 84: 942-959.
Ahmari SE, et al. (2000) Assembly of presynaptic active zones from cytoplasmic transport packets. Nat Neurosci. 3: 445-451.
Ahuja TK, et al. (2007) Hippocampal slice cultures integrated with multi-electrode arrays: A model for study of long-term drug effects on synaptic activity. Drug Development Research. 68: 84-93.
Ainscow EK and Brand MD. (1999) Internal regulation of ATP turnover, glycolysis and oxidative phosphorylation in rat hepatocytes. Eur J Biochem. 266:737-749.
Akaaboune M, et al. (2000) Developmental regulation of amyloid precursor A123. protein at the neuromuscular junction in mouse skeletal muscle. Mol Cell Neurosci. 15: 355-367.
Akanda N, et al. (2008) Effect of malonate, a metabolic pathway inhibitor, on A124. action potential peak shape and the relationship to cellular pathways. 38th Annual Meeting of the Society for Neuroscience. vol. 3 8.
Akanda N, et al. (2009) Analysis of toxin-induced changes in action potential shape for drug development. J Biomol Screen. 14: 1228-1235.
Alabed YZ, et al. (2006) Neuronal responses to myelin are mediated by rho kinase. J Neurochem. 96: 1616-1625.
Albensi BC. (2003) A comparison of drug treatment versus electrical stimulation for suppressing seizure activity. Drug News Perspect. 16: 347-352.
Albert R and Othmer H. (2003) The topology of the regulatory interactions predicts the expression pattern of the segment polarity genes in *Drosophila melanogaster*. J Theor Biol. 223: 1-18.
Albert Y, et al. (2005) Transcriptional regulation of myotube fate specification and intrafusal muscle fiber morphogenesis. J Cell Biol. 169: 257-268.
Alexander SL, et al. (1989) An atomic-resolution atomic-force microscope implemented using an optical lever. J Appl Phys. 65: 164-167.
Al-Shanti N, et al. (2008) Beneficial synergistic interactions of TNF-alpha and IL-6 in C2 skeletal myoblasts—potential cross-talk with IGF system. Growth Factors. 26: 61-73.

Alsina B, et al. (2001) Visualizing synapse formation in arborizing optic axons in vivo: dynamics and modulation by BDNF. Nat Neurosci. 4: 1093-1101.
Alterio J, et al. (1990) Acidic and basic fibroblast growth factor mRNAs are expressed by skeletal muscle satellite cells. Biochem Biophys Res Commun. 166:1205-1212.
Altmann L. (2000) Multielectrode recordings of synaptic plasticity in brain slices: A new method for the assessment of neurotoxic effects. European Journal of Neuroscience. 12: 29-29.
Amarenco P, et al. (2006) High-dose atorvastatin after stroke or transient ischemic attack. N Engl J Med. 355: 549-559.
Amit M. (2007) Feeder-layer free culture system for human embryonic stem cells. Methods Mol Biol. 407: 11-20.
Anderson DJ, et al. (1997) Cell lineage determination and the control of neuronal identity in the neural crest. Cold Spring Harb Symp Quant Biol. 62: 493-504.
Anderson JE, et al. (1991) Distinctive patterns of basic fibroblast growth factor (bFGF) distribution in degenerating and regenerating areas of dystrophic (mdx) striated muscles. Dev Biol. 147: 96-109.
Andersson H and van den Berg A. (2004) Microfabrication and microfluidics for tissue engineering: state of the art and future opportunities. Lab Chip. 4: 98-103.
Antzelevitch C. (2001) Transmural dispersion of repolarization and the T wave. Cardiovasc Res. 50: 426-431.
Antzelevitch C. (2005) Cardiac repolarization. The long and short of it. Europace. 7: 3-9.
Aracil A, et al. (2004) Proceedings of Neuropeptides 2004, the XIV European Neuropeptides Club meeting. Neuropeptides. 38: 369-371.
Archer JD, et al. (2006) Persistent and improved functional gain in mdx dystrophic mice after treatment with L-arginine and deflazacort. F ASEB J. 20:738-740.
Armstrong DL and Rossie S. (1999) Ion channel regulation. Introduction. Adv Second Messenger Phosphoprotein Res. 33: ix-xx.
Arnold HH and Winter B. (1998) Muscle differentiation: more complexity to the network of myogenic regulators. Curr Opin Genet Dev. 8: 539-544.
Arnone MI and Davidson EH. (1997) The hardwiring of development: organization and function of genomic regulatory systems. Development. I24:I85I-I864.
Arsic N, et al. (2004) Vascular endothelial growth factor stimulates skeletal muscle regeneration in vivo. Mol Ther. 10: 844-854.
Askanas V, et al. (1987) De novo neuromuscular junction formation on human muscle fibres cultured in monolayer and innervated by foetal rat spinal cord: ultrastructural and ultrastructural—cytochemical studies. J Neurocytol. 16: 523-537.
Asotra K and Macklin WB. (1993) Protein kinase C activity modulates myelin gene expression in enriched oligodendrocytes. J Neurosci Res. 34: 571-588.
Azzouz M, et al. (2004) VEGF delivery with retrogradely transported lentivector prolongs survival in a mouse ALS model. Nature. 429: 413-41 7.
Badie N, et al. (2009) A method to replicate the microstructure of heart tissue in vitro using DTMRI-based cell micropatterning. Ann Biomed Eng. 37: 2510-2521.
Bahr M, et al. (1991) In vitro myelination of regenerating adult rat retinal ganglion cell axons by Schwann cells. Glia. 4: 529-533.
Baker DC, et al. (2002) The origin and neuronal function of in vivo nonsynaptic glutamate. J Neurosci. 22: 9134-9141.
Bahr M, et al. (1991) In vitro myelination of regenerating adult rat retinal ganglion cell axons by Schwann cells. Glia. 4: 529-533.
Bandi E, et al. (2008) Neural agrin controls maturation of the excitation-contraction coupling mechanism in human myotubes developing in vitro. Am J Physiol Cell Physiol. 294: C66-C73.
Bansal R and Pfeiffer SE. (1992) Novel stage in the oligodendrocyte lineage defined by reactivity of progenitors with R-mAb pnor to QI antigalactocerebroside. J Neurosci Res. 32: 309-3 I 6.
Baraban SC, et al. (1997) Osmolarity modulates K+ channel function on rat AI56. hippocampal interneurons but not CAI pyramidal neurons. J Physiol. 498: 679-689.
Barbulovic-Nad I, et al. (2008) Digital microfluidics for cell-based assays. Lab Chip. 8: 519-526.

(56) References Cited

OTHER PUBLICATIONS

Baron W, et al. (2000) PDGF and FGF-2 signaling in oligodendrocyte progenitor cells: regulation of proliferation and differentiation by multiple intracellular signaling pathways. Mol Cell Neurosci. I5: 314-329.
Barone FC, et al. (I998) Ischemic preconditioning and brain tolerance: temporal histological and functional outcomes, protein synthesis requirement, and interleukin-I receptor antagonist and early gene expression. Stroke. 29: 1937-1950.
Behar TN. (2001) Analysis of fractal dimension of 02A glial cells differentiating in vitro. Methods. 24: 331-339.
Belardinelli L, et al. (2003) Assessing predictors of drug-induced torsade de pointes. Trends Pharmacol Sci. 24: 619-625.
Bellamkonda R, et al. (1995) Hydrogel-based three-dimensional matrix for neural cells. J Biomed Mater Res. 29: 663-671.
Bellas E, et al. (2012) In vitro 3D full-thickness skin-equivalent tissue model using silk and collagen biomaterials. Macromol Biosci. 12: 1627-1236.
Benabid AI. (2003) Deep brain stimulation for Parkinson's disease. Curr Opin Neurobiol. 13: 696-706.
Bender A, et al. (2007) Analysis of pharmacology data and the prediction of adverse drug reactions and off-target effects from chemical structure. ChemMedChem. 2: 861-873.
Bentley A and Atkinsona, A. (2001) Whole cell biosensors—electrochemical and optical approaches to ecotoxicity testing. Toxicol In Vitro. 15: 469-475.
Berg MC, et al. (2004) Controlling mammalian cell interactions on patterned polyelectrolyte multilayer surfaces. Langmuir. 20: 1362-1368.
Berger TW, et al. (2001) Brain-implantable biomimetic electronics as the next era in neural prosthetics. Proceedings of the IEEE. 89: 993-1012.
Bernstein M, et al. (1996) Receptor-mediated calcium signalling in glial cells from mouse corpus callosum slices. J Neurosci Res. 46: 152-163.
Bers DM. (2002) Cardiac excitation-contraction coupling. Nature. 415: 198-205.
Bettinger CJ, et al. (2009) Engineering substrate topography at the micro- and nanoscale to control cell function. Angew Chem Int Ed Engl. 48: 5406-5415.
Bhalla US and Iyengar R. (1999) Emergent properties of networks of biological signaling pathways. Science. 283: 381-387.
Bhat NR, et al. (2007) p38 MAP kinase regulation of oligodendrocyte differentiation with CREB as a potential target. Neurochem Res. 32: 293-302.
Bian WN and Tung L. (2006) Structure-related initiation of reentry by rapid pacing in monolayers of cardiac cells. Circ Res. 98: e29-38.
Biesecker G. (1990) The complement SC5b-9 complex mediates cell adhesion through a vitronectin receptor. J Immunol. 145: 209-214.
Bikfalvi A, et al. (1997) Biological roles of fibroblast growth factor-2. Endocr Rev. 18: 26-45.
Bischoff U, et al. (2000) Effects of fluoroquinolones on HERG currents. Eur J Pharmacol. 406: 341-343.
Bloch-Gallego E, et al. (1991) Survival in vitro of motoneurons identified or purified by novel antibody-based methods is selectively enhanced by musclederived factors. Development. 111: 221-232.
Bodine SC, et al. (2001) Identification of ubiquitin ligases required for skeletal muscle atrophy. Science. 294: 1704-1708.
Bogler O, et al. (1990) Cooperation between two growth factors promotes extended self-renewal and inhibits differentiation of oligodendrocyte-type-2 astrocyte (0-2A) progenitor cells. Proc Natl Acad Sci US A. 87: 6368-6372.
Boillee S, et al. (2006) ALS: a disease of motor neurons and their nonneuronal neighbors. Neuron. 52: 39-59.
Boldin SA and Futerman AH. (2000) Up-regulation of glucosylceramide synthesis upon stimulation of axonal growth by basic fibroblast growth factor. Evidence for post-translational modification of glucosylceramide synthase. J Biol Chem. 275: 9905-9909.
Bordet T, et al. (2001) Protective effects of cardiotrophin-1 adenoviral gene transfer on neuromuscular degeneration in transgenic ALS mice. Hum Mol Genet. 10: 1925-1933.
Bottenstein JE, et al. (1988a) CNS neuronal cell line-derived factors regulate gliogenesis in neonatal rat brain cultures. J Neurosci Res. 20: 291-303.
Bottenstein JE. (1981) Proliferation of glioma cells in serum-free defined medium. Cancer Treat Rep. 65 Suppl 2: 67-70.
Bottenstein JE. (1988b) Advances in vertebrate cell culture methods. Science. 239: G 42, G 48.
Bourgeois EB, et al. (2009) Change in conduction velocity due to fiber curvature in cultured neonatal rat ventricular myocytes. IEEE Trans Biomed Eng. 56: 855-861.
Bousse L. (1996) Whole cell biosensors. Sens Actuators B: Chem. 34: 270-275.
Bowman WC. (2006) Neuromuscular block. Br J Pharmacol. 147 Suppl 1: S277-S286.
Bracciali A, et al. (2008) Stochastic models for the in silico simulation of synaptic processes. BMC Bioinformatics. 9 Suppl 4: S7.
Brand T, et al. (2000) EMBO Workshop Report: Molecular genetics of muscle A191. development and neuromuscular diseases Kloster Irsee, Germany, Sep. 26-Oct. 1, 1999. EMBO J. 19: 1935-1941.
Brand-Saberi B and Christ B. (1999) Genetic and epigenetic control of muscle development in vertebrates. Cell Tissue Res. 296: 199-212.
Brand-Saberi B. (2005) Genetic and epigenetic control of skeletal muscle development. Ann Anat. 187: 199-207.
Bregman BS, et al. (1997) Neurotrophic factors increase axonal growth after spinal cord injury and transplantation in the adult rat. Exp Neurol. 148: 475-494.
Bren-Mattison Y and Olwin BB. (2002) Sonic hedgehog inhibits the terminal A195. differentiation of limb myoblasts committed to the slow muscle lineage. Dev Biol. 242: 130-148.
Brewer GJ, et al. (1993) Optimized survival of hippocampal neurons in B27 supplemented Neurobasal, a new serum-free medium combination. J Neurosci Res. 35: 567-576.
Brewer GJ, et al. (2008) NbActiv4 medium improvement to Neurobasal/B27 increases neuron synapse densities and network spike rates on multielectrode arrays. J Neurosci Methods. 170: 181-187.
Brewer GJ. (1997) Isolation and culture of adult rat hippocampal neurons. J Neurosci Methods. 71: 143-155.
Brewer GJ. (1999) Regeneration and proliferation of embryonic and adult rat hippocampal neurons in culture. Exp Neural. 159: 237-247.
Brito-Martins M, et al. (2008) beta(I)- and beta(2)-adrenoceptor responses in cardiomyocytes derived from human embryonic stem cells: comparison with failing and non-failing adult human heart. Br J Pharmacol. 153: 751-759.
Brockes JP, et al. (1979) Studies on cultured rat Schwann cells. I. Establishment of purified populations from cultures of peripheral nerve. Brain Res. 165: 105-118.
Brokhman I, et al. (2008) Peripheral sensory neurons differentiate from neural precursors derived from human embryonic stem cells. Differentiation. 76: 145-155.
Brumovsky P, et al. (2007) Expression of the vesicular glutamate transporters-I and -2 in adult mouse dorsal root ganglia and spinal cord and their regulation by nerve injury. Neuroscience. 147: 469-490.
Bult CJ, et al. (1996) Complete genome sequence of the methanogenic archaeon, Methanococcus jannaschii. Science. 273: 1058-1073.
Bunge MB, et al. (1962) Electron microscopic demonstration of connections between glia and myelin sheaths in the developing mammalian central nervous system. J Cell Biol. 12: 448-453.
Bunge RP. (1968) Glial cells and the central myelin sheath. Physiol Rev. 48: 197-251.
Bunge RP. (1993) Expanding roles for the Schwann cell: ensheathment, myelination, trophism and regeneration. Curr Opin Neurobiol. 3: 805-809.
Burdick JA and Vunjak-Novakovic G. (2008) Engineered microenvironments for controlled stem cell differentiation. Tissue Eng Part A. 15: 205-219.

(56) References Cited

OTHER PUBLICATIONS

Burgess C, et al. (2008) An endogenous glutamatergic drive onto somatic motoneurons contributes to the stereotypical pattern of muscle tone across the sleep-wake cycle. J Neurosci. 28: 4649-4660.

Butt HJ. (1996) Sensitive Method to Measure Changes in the Surface Stress of Solids. Journal of Colloid and Interface Science. 180: 251-260.

Buzanska L, et al. (2002) Human cord blood-derived cells attain neuronal and glial features in vitro. J Cell Sci. 115: 2131-2138.

Cai J, et al. (2007) Directed differentiation of human embryonic stem cells into functional hepatic cells. Hepatology. 45: 1229-1239.

Caiozzo VJ, at al. (1992) Response of slow and fast muscle to hypothyroidism: maximal shortening velocity and myosin isoforms. Am J Physiol. 263: C86-C94.

Cakir T, et al. (2007) Reconstruction and flux analysis of coupling between metabolic pathways of astrocytes and neurons: application to cerebral hypoxia. Theor Biol Med Model. 4: 48.

Campbell TJ and Williams KM. (2001) Therapeutic drug monitoring: antiarrhythmic drugs. Br J Clin Pharmacol. 52 Suppl 1: 21S-34S.

Camu Wand Henderson CE. (1992) Purification of embryonic rat motoneurons by panning on a monoclonal antibody to the low-affinity NGF receptor. J Neurosci Methods. 44:59-70.

Camu W and Henderson CE. (1994) Rapid purification of embryonic rat motoneurons: an in vitro model for studying MND/ALS pathogenesis. J Neurol Sci. 124 Suppl: 73-74.

Cannon JG. (1998) Intrinsic and extrinsic factors in muscle aging. Ann NY Acad Sci. 854: 72-77.

Caratsch CG, et al. (1994) Interferon-alpha, beta and tumor necrosis factor-alpha enhance the frequency of miniature end-plate potentials at rat neuromuscular junction. Neurosci Lett. 166: 97-100.

Carlsson L. (2006) In vitro and in vivo models for testing arrhythmogenesis in drugs. J Intern Med. 259: 70-80.

Carpenedo RL, et al. (2007) Rotary suspension culture enhances the efficiency, yield, and homogeneity of embryoid body differentiation. Stem Cells. 25: 2224-2234.

Carr PA, et al. (1989) Parvalbumin is highly colocalized with calbindin D28k and rarely with calcitonin gene-related peptide in dorsal root ganglia neurons of rat. Brain Res. 497: 163-170.

Carrasco DI and English AW. Neurotrophin 4/5 is required for the normal development of the slow muscle fiber phenotype in the rat soleus. J Exp Biol. 206: 2191-2200.

Caspi O, et al. (2009) In vitro electrophysiological drug testing using human embryonic stem cell derived cardiomyocytes. Stem Cells Dev. 18: 161-172.

Catoire H, et al. (2008) Sirtuin inhibition protects from the polyalanine muscular dystrophy protein PABPN1. Hum Mol Genet. 17: 2108-2117.

Cerignoli F, et al. (2012) High throughput measurement of Ca2+ dynamics for drug risk assessment in human stem cell-derived cardiomyocytes by kinetic image cytometry. J Pharmacol Toxicol Methods. 66: 246-256.

Chambers SM, et al. (2009) Highly efficient neural conversion of human ES and iPS cells by dual inhibition of SMAD signaling. Nat Biotechnol. 27: 275-280.

Chandran S. et al. (1998) Regional potential for oligodendrocyte generation in the rodent embryonic spinal cord following exposure to EGF and FGF-2. Glia. 24: 382-389.

Chang JC, et al. (2001) Modulation of neural network activity by patterning. Biosens Bioelectron. 16: 527-533.

Charpentier A, et al. (1993) RRR-alpha-tocopheryl succinate inhibits proliferation and enhances secretion of transforming growth factor-beta (TGFbeta) by human breast cancer cells. Nutr Cancer. 19: 225-239.

Chaudhary KW, et al. (2006) Embryonic stem cells in predictive cardiotoxicity: laser capture microscopy enables assay development. Toxicol Sci. 90: 149-158.

Chaves M, et al. (2005) Robustness and fragility of Boolean models for genetic regulatory networks. J Theor Biol. 235: 431-449.

Chaves M, et al. (2006) Methods of robustness analysis for Boolean models of gene control networks. Syst Biol (Stevenage). 153: 154-167.

Chen CS, et al. (1997) Geometric control of cell life and death. Science. 276: 1425-1428.

Chen EW, et al. (1995) Target regulation of a motor neuron-specific epitope. J Neurosci. 15: 1555-1566.

Chen J and von Bartheld CS. (2004) Role of exogenous and endogenous trophic factors m the regulation of extraocular muscle strength during development.Invest Ophthalmol Vis Sci. 45: 3538-3545.

Chen QS, et al. (2000) Impairment of hippocampal long-term potentiation by Alzheimer amyloid beta-peptides. J Neurosci Res. 60: 65-72.

Chen X, et al. (2005) Dedifferentiation of adult human myoblasts induced by ciliary neurotrophic factor in vitro. Moll Biol Cell. 16: 3140-3151.

Chen XF, et al. (2008) Dynamic simulation of the effect of calcium-release activated calcium channel on cytoplasmic Ca2+ oscillation. Biophys Chem. 136: 87-95.

Chen XP, (2003) Exogenous rhCNTF inhibits myoblast differentiation of skeletal muscle of adult human in vitro. Sheng Li Xue Bao. 55: 464-468.

Chiu A Y, et al. (1993) A motor neuron-specific epitope and the low-affinity nerve growth factor receptor display reciprocal patterns of expression during development, axotomy, and regeneration. J Comp Neurol. 328: 351-363.

Choi-Lundberg DL and Bohn MC. (1995) Ontogeny and distribution of glial cell line-derived neurotrophic factor (GDNF) mRNA in rat. Brain Res Dev Brain Res. 85: 80-88.

Choudhury A, et al. (2007) A piezoresistive microcantilever array for surface stress measurement: curvature model and fabrication. J Micromech Microeng. 17: 2065-2076.

Chow I and Poo MM. (1985) Release of acetylcholine from embryonic neurons upon contact with muscle cell. J Neurosci. 5: 1076-1082.

Christ B and Brand-Seberi B. (2002) Limb muscle development. Int J Dev Biol. 46: 905-914.

Chua SJ, et al. (2009) Neural progenitors, neurons and oligodendrocytes from human umbilical cord blood cells in a serum-free, feeder-free cell culture. Biochem Biophys Res Commun. 379(2):217-221.

Cizkova D, et al. (2007) Functional recovery in rats with ischemic paraplegia after spinal grafting of human spinal stem cells. Neuroscience. 147: 546-560.

Clegg CH, et al. (1987) Growth factor control of skeletal muscle differentiation: commitment to terminal differentiation occurs in G1 phase and is repressed by fibroblast growth factor. J Cell Biol. 105: 949-956.

Clements JD, et al. (1992) The time course of glutamate in the synaptic cleft. Science. 258: 1498-1501.

Coggan JS, et al. (2005) Evidence for ectopic neurotransmission at a neuronal synapse. Science. 309: 446-451.

Cohen RI and Almazan G. (1993) Norepinephrine-stimulated PI hydrolysis in oligodendrocytes is mediated by alpha IA-adrenoceptors. Neuroreport. 4: 1115-1118.

Cohen-Cory S. (2002) The developing synapse: construction and modulation of synaptic structures and circuits. Science. 298: 770-776.

Collins CA and Morgan JE. (2003) Duchenne's muscular dystrophy: animal models used to investigate pathogenesis and develop therapeutic strategies. Int J Exp Pathol. 84: 165-172.

Colomar A and Robitaille R. (2004) Glial modulation of synaptic transmission at the neuromuscular junction. Glia. 4 7: 284-289.

Cooper A, et al. (1976) The growth of mouse neuroblastoma cells in controlled orientations on thin films of silicon monoxide. Exp Cell Res. 103: 435-439.

Corey JM, et al. (1991) Compliance of hippocampal neurons to patterned substrate networks. J Neurosci Res. 30: 300-307.

Corey JM, et al. ( 1996) Micrometer resolution silane-based patterning of hippocampal neurons: critical variables in photoresist and laser ablation processes for substrate fabrication. IEEE Trans Biomed Eng. 43: 944-955.

(56) References Cited

OTHER PUBLICATIONS

Corey JM, et al. (1997) Differentiated B 104 neuroblastoma cells are a highresolution assay for micropatterned substrates. J Neurosci Methods. 75: 91-97.

Cortassa S. et al. (2003) An integrated model of cardiac mitochondrial energy metabolism and calcium dynamics. Biophys J. 84: 2734-2755.

Cossu G, et al. (1996) How is myogenesis initiated in the embryo? Trends Genet. 12: 218-223.

Courdier-Fruh I, et al. (2002) Glucocorticoid-mediated regulation of utrophin levels in human muscle fibers. Neuromuscul Disord. 12(Suppl 1): S95-S104.

Cross-Doersen D and Isfort RJ. (2003) A novel cell-based system for evaluating skeletal muscle cell hypertrophy-inducing agents. In Vitro Cell Dev Biol Animal. 39: 407-412.

Cukierman E, et al. (2002) Cell interactions with three-dimensional matrices. Curr Opin Cell Biol. 14: 633-639.

Cunningham JJ and Roussel MF. (2001) Cyclin-dependent kinase inhibitors in the development of the central nervous system. Cell Growth Differ. 12: 387-396.

Cuppini R, et al. (2001) Alpha-tocopherol controls cell proliferation in the adult rat dentate 12:vrus. Neurosci Lett. 303: 198-200.

Currie PD and Ingham PW. (1996) Induction of a specific muscle cell type by a hedgehog-like protein in zebrafish. Nature. 382: 452-455.

Curtis R, et al. (1988) Development of macroglial cells in rat cerebellum. I. Use of antibodies to follow early m VIVO development and migration of oligodendrocytes. J Neurocytol. 17: 43-54.

Cysyk J and Tung L. (2008) Electric field perturbations of spiral waves attached to millimeter-size obstacles. Biophys J. 94: 1533-1541.

Dakhel Y and Jamali F. (2006) Erythromycin potentiates PR interval prolonging effect of verapamil in the rat: a pharmacodynamic drug interaction. Toxicol Appl Pharmacol. 214: 24-29.

Daniels MP, et al. (2000) Rodent nerve-muscle cell culture system for studies of neuromuscular junction development: refinements and applications. Microsc Res Tech. 49: 26-37.

Daniels MP. (1990) Localization of actin, beta-spectrin, 43×10(3) Mr and 58×10(3) Mr proteins to receptor-enriched domains of newly formed acetylcholine receptor aggregates in isolated myotube membranes. J Cell Sci. 97(Pt 4): 615-626.

Daniels MP. (1997) Intercellular communication that mediates formation of the neuromusculariunction. Mol Neurobiol. 14: 143-170.

Das M, et al. (2003) Electrophysiological and morphological characterization of rat embryonic motoneurons in a defined system. Biotechnol Prog. 19: 1756-1761.

Das M, et al. (2004) Long-term culture of embryonic rat cardiomyocytes on an organosilane surface in a serum-free medium. Biomaterials. 25: 5643-5647.

Das M, et al. (2005) Adult rat spinal cord culture on an organosilane surface in a novel serum-free medium. In Vitro Cell Dev Biol Anim. 41: 343-348.

Das M, et al. (2006) a defined system to allow skeletal muscle differentiation and subsequent integration with silicon microstructures. Biomaterials. 27: 4374-4380.

Das M, et al. (2007a) Auto-catalytic ceria nanoparticles offer neuroprotection to adult rat spinal cord neurons. Biomaterials. 28: 1918-1925.

Das M, et al. (2007b) Differentiation of skeletal muscle and integration of myotubes with silicon microstructures using serum-free medium and a synthetic silane substrate. Nat Protoc. 2: 1795-1801.

Das M, et al. (2007c) Embryonic motoneuron-skeletal muscle co-culture in a defined system. Neuroscience. 146: 481-488.

Das M, et al. (2008) Temporal neurotransmitter conditioning restores the functional activity of adult spinal cord neurons in long-term culture. Exp Neurol. 209: 171-180.

Das M, et al. (2009a) Developing a novel serum-free cell culture model of skeletal muscle differentiation by systematically studying the role of different growth factors in myotube formation. In Vitro Cell Dev Biol Anim. 45: 378-387.

Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.

Das M, et al. (2010) A defined long-term in vitro tissue engineered model of neuromuscular junctions. Biomaterials. 31: 4880-4888.

Datar R, et al. (2009) Cantilever Sensors: Nanomechanical Tools for Diagnostics. MRS Bulletin. 34: 449-454.

David JA and Pitman RM. (1982) The effects of axotomy upon the extrasynaptic acetylcholine sensitivity of an identified motoneurone m the cockroach Periplaneta americana. J Exp Biol. 98: 329-341.

Davis H, et al. (2012) Rat Cortical Oligodendrocyte-Embryonic Motoneuron Co-Culture: An In Vitro Axon-Oligodendrocyte Interaction Model. J Biomater Tissue Eng. 2: 206-214.

Davis H, et al. (2012) Small Molecule Induction of Human Umbilical Stem Cells into MBP-positive Oligodendrocytes in a Defined Three-Dimensional Environment. ACS Chem Neurosci. 3(1):31-39.

De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.

De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.

de Lange P. et al. (2006) Sequential changes in the signal transduction responses of skeletal muscle following food deprivation. FASEB J. 20: 2579-2581.

de Wilde J, et al. (2008) Short-term high fat-feeding results in morphological and metabolic adaptations m the skeletal muscle of C57BL/6J mice. Physiol Genomics. 32: 360-369.

Dell'Era P, et al. (2003) Fibroblast growth factor receptor-I is essential for in vitro cardiomyocyte development. Circ Res. 93: 414-420.

Denning C and Anderson D. (2008) Cardiomyocytes from human embryonic A291. stem cells as predictors of cardiotoxicity. Drug Discovery Today: Therapeutic Strategies. 5: 223-232.

Dennis RG and Kosnik IPE. (2000) Excitability and isometric contractile A292. properties of mammalian skeletal muscle constructs engineered in vitro. In Vitro Cell Dev Biol Anim. 36: 327-335.

Dennis RG, et al. (2001) Excitability and contractility of skeletal muscle A293. engineered from primary cultures and cell lines. Am J Physiol Cell Physiol. 280: C288-C295.

Denyer MCT, et al. (1998) Preliminary study on the suitability of a A294. pharmacological bio-assay based on cardiac myocytes cultured over microfabricated microelectrode arrays. Med Biol Eng Coniput. 36: 638-644.

Descarries L, et al. (1997) Diffuse transmission by acetylcholine in the CNS. Prog Neurobiol. 53: 603-625.

Dhvan Rand Tsai L. (2001) A decade of CDK5. Nat Rev Mol Cell Biol. 2: 749-759.

Dhir V, et al. (2009) Patterning of diverse mammalian cell types in serum free medium with photoablation. Biotechnol Prog. 25: 594-603.

Di Giovanni S. et al. (2005) Cell cycle inhibition provides neuroprotection and reduces glial proliferation and scar formation after traumatic brain injury. Proc Natl Acad Sci U SA. 102: 8333-8338.

Dimitrova DS and Gilbert DM. (2000) Temporally coordinated assembly and disassembly of replication factories in the absence of DNA synthesis. Nat Cell Biol. 2: 686-694.

Djouhri L and Lawson SN. (1999) Changes in somatic action potential shape in guinea-pig nociceptive primary afferent neurones during inflammation in vivo. J Physiol. 520 Pt 2: 565-576.

Dolcet X, et al. (2001) Cytokines promote motoneuron survival through the Janus kinase-dependent activation of the phosphatidylinositol 3-kinase pathway. Mol Cell Neurosci. 18: 619-631.

(56) References Cited

OTHER PUBLICATIONS

Du Y, et al. (2006) Distinct effects of p75 in mediating actions of neurotrophins on basal forebrain oligodendrocytes. Mol Cell Neurosci. 31: 366-375.

Dulcey CS, et al. (1991) Deep UV photochemistry of chemisorbed monolayers: patterned coplanar molecular assemblies. Science. 252: 551-554.

Dumont RJ, et al. (2001) Acute spinal cord injury, part I: pathophysiologic mechanisms. Clin Neuropharmacolo12:v. 24: 254-264.

Duport S, et al. (1999) A metallic multisite recording system designed for continuous long-term monitoring of electrophysiological activity in slice cultures. Biosens Bioelectron. 14: 369-376.

Dusterhoft S and Pette D. (1999) Evidence that acidic fibroblast growth factor promotes maturation of rat satellite-cell-derived myotubes m vitro. Differentiation. 65: 161-169.

Dutton EK, et al. (1995) Acetylcholine receptor aggregation at nerve-muscle contacts in mammalian cultures: induction by ventral spinal cord neurons is specific to axons. J Neurosci. 15: 7401-7416.

Edwards D, et al. (2010) Addition of glutamate to serum-free culture promotes recovery of electrical activity in adult hippocampal neurons in vitro. J Neurosci Methods. 190: 155-163.

Egert U, et al. (1998) A novel organotypic long-term culture of the rat hippocampus on substrate-integrated multielectrode arrays. Brain Res Brain Res Protoc. 2: 229-242.

Egert U, et al. (2006) Analysis of cardiac myocyte activity dynamics with microeletrode arrays. In: Taketani M BM, editor. Advances m netwrok electrophysiology using multi electrode arrays: Springer 2006. p. 274-290.

Eisen A and Swash M. (2001) Clinical neurophysiology of ALS. Clin Neurophysiol. 112: 2190-2201.

Eisenberg T, et al. (2009) Induction of autophagy by spermidine promotes longevity. Nat Cell Biol. 11: 1305-1314.

Eldridge CF, et al. (1989) Differentiation of axon-related Schwann cells in vitro: II. Control of myelin formation by basal lamina. J Neurosci. 9: 625-638.

Elia D, et al. (2007) Sonic hedgehog promotes proliferation and differentiation of adult muscle cells: Involvement of MAPK/ERK and PI3K/ AKT pathways. Biochim Biophys Acta. 1773: 1438-1446.

Emery AEH. (2002) The muscular dystrophies. Lancet. 359: 687-695.

Engler AJ, et al. (2006) Matrix elasticity directs stem cell lineage specification. Cell. 126: 677-689.

English AW. (2003) Cytokines, growth factors and sprouting at the neuromuscular junction. J Neurocytol. 32: 943-960.

Entcheva EK, et al. (2004) Fluorescence imaging of electrical activity in cardiac cells using an all-solid-state system. IEEE Trans Biomed Eng. 51: 331-341.

Ericson J, et al. (1992) Early stages of motor neuron differentiation revealed by expression ofhomeobox gene Islet-I. Science. 256: 1555-1560.

Esch MB, et al. (2011) The role of body-on-a-chip devices in drug and toxicity studies. Annu Rev Biomed Eng. 13: 55-72.

Esch MB, et al. (2012) On chip porous polymer membranes for integration of gastrointestinal tract epithelium with microfluidic 'body-on-a-chip' devices. Biomed Microdevices. 14: 895-906.

Eschenhagen T and Zimmermann WH. (2005) Engineering myocardial tissue. Circ Res. 97: 1220-1231.

Evans MS, et al. (1998) Electrophysiology of embryonic, adult and aged rat hippocampal neurons in serum-free culture. J Neurosci Methods. 79: 37-46.

Fan CM and Tessier-Lavigne M. (1994) Patterning of mammalian somites by surface ectoderm and notochord: evidence for sclerotome induction by a hedgehog homolog. Cell. 79: 1175-1186.

Faraut B, et al. (2004) Thrombin reduces MuSK and acetylcholine receptor expression along with neuromuscular contact size in vitro. Eur J Neurosci. 19: 2099-2108.

FDA (2004) Innovation or Stagnation: Challenge and Opportunity on the Critical Path to New Medical Products.

Fernandez-Valle C, et al. (1993) Expression of the protein zero myelin gene in axon-related Schwann cells is linked to basal lamina formation. Development. 119: 867-880.

Fernandez-Valle C, et al. (1995) Schwann cells degrade myelin and proliferate in the absence of macrophages: evidence from in vitro studies of Wallerian degeneration. J Neurocytol. 24: 667-679.

Fields GB, et al. (1998) Protein-like molecular architecture: biomaterial applications for inducing cellular receptor binding and signal transduction. Biopolymers. 47: 143-151.

Fields GB. (1999) Induction of protein-like molecular architecture by selfassembly processes. Bioorg Med Chem. 7: 75-81.

Figenschou A, et al. (1996) Cholinergic modulation of the action potential in rat hippocampal neurons. Eur J Neurosci. 8:211-219.

Fink CC, et al. (1999) Determination of time-dependent inositol-1,4,5-trisphosphate concentrations during calcium release in a smooth muscle cell. Biophys J. 77: 617-628.

Fischbach GD and Cohen SA. (1973) The distribution of acetylcholine sensitivity over uninnervated and innervated muscle fibers grown in cell culture. Dev Biol. 31: 147-162.

Fischbach GD. (1972) Synapse formation between dissociated nerve and muscle cells in low density cell cultures. Dev Biol. 28: 407-429.

Fisher OZ, et al. (2010) Bioinspired materials for controlling stem cell fate. Ace Chem Res. 43: 419-428.

Fishman RA. (2002) The cerebrospinal fluid production rate is reduced in dementia of the Alzheimer's type. Neurology. 58: 1866; author reply 1866.

Flucher BE, et al. (1990) Localization of the alpha 1 and alpha 2 subunits of the dihydropyridine receptor and ankyrin in skeletal muscle triads. Neuron. 5:339-351.

Flucher BE, et al. (1991) Biogenesis of transverse tubules in skeletal muscle in vitro. Dev Biol. 145: 77-90.

Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.

Flucher BE, et al. (1994) Molecular organization of transverse tubule/sarcoplasmic reticulum junctions during development of excitationcontraction coupling in skeletal muscle. Mol Biol Cell. 5: 1105-1118.

Forry SP, et al. (2006) Facilitating the culture of mammalian nerve cells with polyelectrolyte multilayers. Langmuir. 22: 5770-5775.

Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.

Fowler VM, et al. (1993) Tropomodulin is associated with the free (pointed) ends of the thin filaments in rat skeletal muscle. J Cell Biol. 120: 411-420.

Fox MA, et al. (2007) Distinct target-derived signals orgamze formation, maturation, and maintenance of motor nerve terminals. Cell. 129: 179-193.

Francis PT. (2008) Glutamatergic approaches to the treatment of cognitive and behavioural symptoms of Alzheimer's disease. Neurodegener Dis. 5: 241-243.

Frank E and Fischbach GD. (1979) Early events in neuromuscular junction formation in vitro: induction of acetylcholine receptor clusters in the postsynaptic membrane and morphology of newly formed synapses. J Cell Biol. 83: 143-158.

Franzini-Armstrong C and Protasi F. (1997) Ryanodine receptors of striated muscles: a complex channel capable of multiple interactions. Physiol Rev. 77: 699-729.

Friedman B, et al. (1995) BDNF and NT-4/5 exert neurotrophic influences on injured adult spinal motor neurons. J Neurosci. 15: 1044-1056.

Fu X, et al. (1995) Acidic fibroblast growth factor reduces rat skeletal muscle damage caused by ischemia and reperfusion. Chin Med J (Engl). 108: 209-214.

Fuentes-Medel Y, et al. (2012) Integration of a retrograde signal during synapse formation by glia-secreted TGF-B ligand. Curr Biol. 22: 1831-1838.

(56) References Cited

OTHER PUBLICATIONS

Funakoshi H, et al. (1995) Muscle-derived neurotrophin-4 as an activitydependent trophic signal for adult motor neurons. Science. 268: 1495-1499.
Gaztanaga L, et al. (2012) Mechanisms of cardiac arrhythmias. Rev Esp Cardiol (Engl Ed). 65(2): 174-85.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175:50-57.
Galizia CG and Menzel R. (2000) Probing the olfactory code. Nat Neurosci. 3: 853-854.
Gao BX and Ziskind-Conhaim L. (1995) Development of glycine- and GABAgated currents in rat spinal motoneurons. J Neurophysiol. 74: 113-121.
Gao Bx and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69:4027-4037.
Gaud A, et al. (2004) Prednisone reduces muscle degeneration in dystrophindeficient Caenorhabditis elegans. Neuromuscul Disord. 14: 365-370.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.
Ghiani CA, et al. (1999) Neurotransmitter receptor activation triggers p27(Kipl) and p21(CIP 1) accumulation and G 1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry. 13: 1052-1061.
Glass Land Kauffman SA. (1973) The logical analysis of continuous, non-linear biochemical control networks. J Theor Biol. 39: 103-129.
Glass L. (1975) Classification of biological networks by their qualitative dynamics. J Theor Biol. 54: 85-107.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.
Golden JP, et al. (1999) Expression of neurturin, GDNF, and GDNF family-receptor mRNA in the developing and mature mouse. Exp Neurol. 158: 504-528.
Gonzalez AM, et al. (1990) Distribution of basic fibroblast growth factor in the 18-day rat fetus: localization in the basement membranes of diverse tissues. J Cell Biol. 110: 753-765.
Goodyear S and Sharma MC. (2007) Roscovitine regulates invasive breast cancer cell (MDA-MB231) proliferation and survival through cell cycle regulatory protein cdk5. Exp Mol Pathol. 82: 25-32.
Goodyear S. (2005) Roscovitine induced cell death is mediated through specific inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gozes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P. et al. (2004) First dose of potential new medicines to humans: how animals help. Nat Rev Drug Discov. 3: 226-236.
Greenstein JL and Winslow RL (2002) An integrative model of the cardiac ventricular myocyte incorporating local control of Ca2+ release. Biophys J. 83:2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use ofNeuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374:1745-175.
Guettier-Sigrist S, et al. (1998) Muscle could be the therapeutic target in SMA treatment. J Neurosci Res. 53: 663-669.
Guettier-Sigrist S, et al. (2000) Cell types required to efficiently innervate human muscle cells in vitro. Exp Cell Res. 259: 204-212.
Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.
Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNPI. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.
Gureviciene I, et al. (2004) Normal induction but accelerated decay of LTP in APP+ PSI transgenic mice. Neurobiol Dis. 15: 188-195.
Haas HL and Selbach 0. (2000) Functions of neuronal adenosine receptors. Naunyn Schmiedebergs Arch Pharmacol. 362: 375-381.

(56) References Cited

OTHER PUBLICATIONS

Halbach M, et al. (2003) Estimation of action potential changes from field potential recordings in multicellular mouse cardiac myocyte cultures. Cell Physiol Biochem. 13: 271-284.
Hall BK and Miyake T. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.
Han DK and Hubbell JA. (1997) Synthesis of Polymer Network Scaffolds from 1-Lactide and Poly( ethylene glycol) and Their Interaction with Cells. Macromolecules. 30: 607—6083.
Hantai D, et al. (1991) Developmental appearance of thrombospondin in neonatal mouse skeletal muscle. Eur J Cell Biol. 55: 286-294.
Harding SE, et al. (2007) The human embryonic stem cell-derived cardiomyocyte as a pharmacological model. Pharmacol Ther. 113: 341-353.
Hardy J and Selkoe DJ. (2002) The amyloid hypothesis of Alzheimer's disease: progress and problems on the road to therapeutics. Science. 297: 353-356.
Hari L, et al. (2002) Lineage-specific requirements of beta-catenin in neural crest development. J Cell Biol. 159: 867-880.
Harms H, et al. (2006) Whole-cell living biosensors—are they ready for environmental application? Appl Microbiol Biotechnol. 70: 273-280.
Harper JM, et al. (2004) Axonal growth of embryonic stem cell-derived motoneurons in vitro and in motoneuron-injured adult rats. Proc Natl Acad Sci U s A. 101: 7123-7128.
Harsch A, et al. (1997) Strychnine analysis with neuronal networks in vitro: extracellular array recording of network responses. Biosens Bioelectron. 12: 827-835.
Heiduschka P and Thanos S. (1998) Implantable bioelectric interfaces for lost nerve functions. Prog Neurobiol. 55: 433-461.
Heinrich G. (2003) A novel BDNF gene promoter directs expression to skeletal muscle. BMC Neurosci. 4: 11.
Henderson CE, et al. (1993) Neurotrophins promote motor neuron survival and are present in embryonic limb bud. Nature. 363: 266-270.
Henderson CE, et al. (1994) GDNF: a potent survival factor for motoneurons present in peripheral nerve and muscle. Science. 266: 1062-1064.
Hennessey JV, et al. (1997) Increase in percutaneous muscle biopsy yield with a suction-enhancement technique. J Appl Physiol. 82: 1739-1742.
Hennessey N, et al. (2001) Growth hormone administration and exercise effects on muscle fiber type and diameter in moderately frail older people. J Am Geriatr Soc. 49: 852-858.
Hermann M, et al. (2006) Exposure of atorvastatin is unchanged but lactone and acid metabolites are increased several-fold in patients with atorvastatin-induced myopathy. Clin Pharmacol Ther. 79: 532-539.
Herrup K and Yang Y. (2007) Cell cycle regulation in the postmitotic neuron: oxymoron or new biology? Nat Rev Neurosci. 8: 368-378.
Hickman J, et al. (1993) The use of monlayers as templates for biocompatibility studies. Abstracts of Papers of the American Chemical Society. 205: 146-Coll.
Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.
Hickman JJ, et al. (1994) Rational Pattern Design for in-Vitro Cellular Networks Using Surface Photochemistry. J Vac Science Technol A. 12: 607-616.
Hirano A. ( 1968) A confirmation of the oligodendroglial origin of myelin in the adult rat. J Cell Biol. 38: 637-640.
Hjerling-Leffler J, et al. (2005) The boundary cap: a source of neural crest stem cells that generate multiple sensory neuron subtypes. Development. 132: 2623-2632.
Hoffman EP and Escolar D. (2006) Translating mighty mice into neuromuscular therapeutics: is bigger muscle better? Am J Pathol. 168: 177 5-1778.
Hoffmann F and Bading H. (2006) Long term recordings with microelectrode arrays: studies of transcription-dependent neuronal plasticity and axonal regeneration. J Physiol Paris. 99: 125-132.
Holleran AL, et al. (1995) Glutamine metabolism in AS-30D hepatoma cells. Evidence for its conversion into lipids via reductive carboxylation. Mol Cell Biochem. 152: 95-101.
Hondeghem LM and Hoffinan P. (2003b) Blinded test in isolated female rabbit heart reliably identifies action potential duration prolongation and proarrhythmic drugs: importance of triangulation, reverse use dependence, and instability. J Cardiovasc Pharmacol. 41: 14-24.
Hondeghem LM, et al. (2001) Instability and triangulation of the action potential predict serious proarrhythmia, but action potential duration prolongation is antiarrhythmic. Circulation. 103: 2004-2013.
Hondeghem LM, et al. (2003a) Detection of proarrhythmia in the female rabbit heart: blinded validation. J Cardiovasc Electrophysiol. 14: 287-29.
Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.
Hondeghem LM. (2007) Relative contributions of TRiaD and QT to proarrhythmia. J Cardiovasc Electrophysiol. 18: 655-657.
Hsiao CF, et al. (2005) Voltage-dependent calcium currents in trigeminal motoneurons of early postnatal rats: modulation by 5-HT receptors. J Neurophysiol. 94: 2063-2072.
Hu BY, et al. (2009) Human oligodendrocytes from embryonic stem cells: conserved SHH signaling networks and divergent FGF effects. Development. 136: 1443-1452.
Hua JY and Smth SJ. (2004) Neural activity and the dynamics of central nervous system development. Nat Neurosci. 7: 327-332.
Huang Y, et al. (2007) An alphaIA-adrenergic-extracellular signal-regulated kinase survival signaling pathway in cardiac myocytes. Circulation. 115: 763-772.
Huang YC, et al. (2005) Rapid formation of functional muscle in vitro using fibrin gels. J Appl Physiol. 98: 706-713.
Hucka M, et al. (2003) The systems biology markup language (SBML): a medium for representation and exchange of biochemical network models. Bioinformatics. 19: 524-531.
Hughes B. (2008) 2007 FDA drug approvals: a year of flux. Nat Rev Drug Discov. 7: 107-109.
Huh D, et al. (2010) Reconstituting organ-level lung functions on a chip. Science. 328: 1662-1668.
Huh D, et al. (2012) Microengineered physiological biomimicry: organs-onchips. Lab Chip. 12: 2156-2164.
Hui EE and Bhatia SN. (2007) Microscale control of cell contact and spacing via three-component surface patterning. Langmuir. 23: 4103-4107.
Hung SC, et al. (2002) In vitro differentiation of size-sieved stem cells into electrically active neural cells. Stem Cells. 20: 522-529.
Husmann I, et al. (1996) Growth factors in skeletal muscle regeneration. Cytokine Growth Factor Rev. 7: 249-258.
Huxley, A. F. (1975). The origin of force in skeletal muscle. Ciba Found Symp. 31: 271-290.
Ichikawa H, et al. (2004) Effect of Bm-3a deficiency on parvalbumin-immunoreactive primary sensory neurons in the dorsal root ganglion. Brain Res Dev Brain Res. 150: 41-45.
Inoue N, et al. (2004) Rapid electrical stimulation of contraction modulates gap junction protein m neonatal rat cultured cardiomyocytes: involvement of mitogen-activated protein kinases and effects of angiotensin II-receptor antagonist. J Am Coll Cardiol. 44: 914-922.

(56) References Cited

OTHER PUBLICATIONS

Iravanian S. et al. (2003) Functional reentry in cultured monolayers of neonatal rat cardiac cells. Am J Physiol Heart Circ Physiol. 285: H449-H456.
Ito Y. (1999) Surface micropatterning to regulate cell functions. Biomaterials. 20:2333-2342.
Izrael M, et al. (2007) Human oligodendrocytes derived from embryonic stem cells: Effect of noggin on phenotypic differentiation in vitro and on myelination in vivo. Mol Cell Neurosci. 34: 310-323.
Izumiya Y, et al. (2008) Fast/glycolytic muscle fiber growth reduces fat mass and improves metabolic parameters in obese mice. Cell Metabolism. 7: 159-172.
Jackson JH 4th, et al. (2004) Assessment of drug therapy management and the prevalence of heart failure in a managed care population with hypertension. J Manag Care Pharm. 10: 513-520.
Jaworska-Wilczynska M, et al. (2002) Three lipoprotein receptors and cholesterol in inclusion-body myositis muscle. Neurology. 58: 438-445.
Jensen J, et al. (2009) Human embryonic stem cell technologies and drug discovery. J Cell Physiol. 219: 513-519.
Jessen KR and Mirsky R. (2005) The origin and development of glial cells in peripheral nerves. Nat Rev Neurosci. 6: 671-682.
Jevsek M, et al. (2004) Origin of acetylcholinesterase in the neuromuscular junction formed in the in vitro innervated human muscle. Eur J Neurosci. 20:2865-2871.
Jhamandas JH, et al. (2001) Cellular mechanisms for amyloid beta-protein activation of rat cholinergic basal forebrain neurons. J Neurophysiol. 86: 1312-1320.
Jiang XH, et al. (2009) Isolation and characterization of neural crest stem cells derived from in vitro-differentiated human embryonic stem cells. Stem Cells Dev. 18: 1059-1070.
Jiang Z and Clemens PR. (2006) Cellular caspase-8-like inhibitory protein (cFLIP) prevents inhibition of muscle cell differentiation induced by cancer cells. FASEB J. 20: 2570-2572.
Jiang ZG, et al. (1990) Excitatory and inhibitory transmission from dorsal root afferents to neonate rat motoneurons in vitro. Brain Res. 535: 110-118.
Jin P, et al. (1991) Recombinant platelet-derived growth factor-BB stimulates growth and inhibits differentiation of rat L6 myoblasts. J Biol Chem. 266: 1245-1249.
Johnson TE, et al. (2005) Statins and PP ARalpha agonists induce myotoxicity in differentiated rat skeletal muscle cultures but do not exhibit synergy with cotreatment. Toxicol Appl Pharmacol. 208: 210-221.
Julius D and Basbaum AI. (2001) Molecular mechanisms of nociception. Nature. 413: 203-210.
Jung DR, et al. (1998) Cell-Based Sensor Microelectrode Array Characterized by Imaging X-ray Photoelectron Spectroscopy, Scanning Electron Microscopy, /mpedance Measurements, and Extracellular Recordings. Journal of Vacuum Science & Technology A (Vacuum, Surfaces, and Films). 16: 1183-1188.
Jung DR, et al. (2001) Topographical and physicochemical modification of material surface to enable patterning of living cells. Crit Rev Biotechnol. 21: 111-154.
Jurdana M, et al. (2009) Neural agrin changes the electrical properties of developing human skeletal muscle cells. Cell Mol Neurobiol. 29: 123-131.
Kaeberlein M. (2009) Spermidine surprise for a long life. Nat Cell Biol. 11:1277-1278.
Kaji H, et al. (2003) Pharmacological characterization of micropatterned cardiac myocytes. Biomaterials. 24: 4239-4244.
Kamp TJ. (2009) Human pluripotent stem cell-derived card iomyocytes for safety pharmacology applications. Journal of Pharmacological and Toxicological Methods. 60: 259.
Kane RS, et al. (1999) Patterning proteins and cells using soft lithography. Biomaterials. 20: 2363-2376.
Kang JH, et al. (2009) In vitro 3D model for human vascularized adipose tissue. Tissue Eng Part A. 15: 2227-2236.
Kato AC and Lindsay RM. (1994) Overlapping and additive effects of neurotrophins and CNTF on cultured human spinal cord neurons. Exp Neurol. 130: 196-20.
Katsuki H, et al. (2000) Distinct signaling pathways involved in multiple effects of basic fibroblast growth factor on cultured rat hippocampal neurons. Brain Res. 885: 240-250.
Katz LC and Shatz CJ. (1996) Synaptic activity and the construction of cortical circuits. 274: 1133-1138.
Kauffman S, et al. (2003) Random Boolean network models and the yeast transcriptional network. Proc Natl Acad Sci US A. 100: 14796-14799.
Kauffman S. (1971) Gene regulation networks: a theory for their global structure and behaviors. Curr Top Dev Biol. 6: 145-182.
Kaufmann P. et al. (2006) Toxicity of statins on rat skeletal muscle mitochondria. Cell Mol Life Sci. 63: 2415-2425.
Keefer EW, et al. (2001) Acute toxicity screening of novel AChE inhibitors using neuronal networks on microelectrode arrays. Neurotoxicology. 22: 3-1.
Keefer EW, et al. (2001) Characterization of acute neurotoxic effects of trimethylolpropane phosphate via neuronal network biosensors. Biosens Bioelectron. 16: 513-525.
Kessaris N, et al. (2008) Specification of CNS glia from neural stem cells in the embryonic neuroepithelium. Philos Trans R Soc Lond B Biol Sci. 363: 71-85.
Khademhosseini A, et al. (2006a) Interplay of biomaterials and micro-scale technologies for advancing biomedical applications. J Biomater Sci Polym Ed. 17: 1221-1240.
Khademhosseini A, et al. (2006b) Microscale technologies for tissue engineering and biology. Proc Natl Acad Sci USA. 103: 2480-2487.
Khorchid A, et al. (1999) Characterization of the signal transduction pathways mediating noradrenaline-stimulated MAPK activation and c-fos expression in oligodendrocyte progenitors. JNeurosci Res. 58: 765-778.
Khorchid A, et al. (2002) Developmental regulation of alpha IA-adrenoceptor function in rat brain oligodendrocyte cultures. Neuropharmacology. 42: 685-696.
Kidambi S. et al. (2004) Controlling primary hepatocyte adhesion and spreading on protein-free polyelectrolyte multilayer films. J Am Chem Soc. 126: 16286-16287.
Kidambi S, et al. (2007a) Patterned co-culture of primary hepatocytes and fibroblasts using polyelectrolyte multilayer templates. Macromol Biosci. 7: 344-353.
Kidambi S, et al. (2007b) Cell adhesion on polyelectrolyte multilayer coated polydimethylsiloxane surfaces with varying topographies. Tissue Eng. 13: 2105-2117.
Kidd, J. (2006). Life after statin patent expiries. Nat Rev Drug Discov. 5: 813-814.
Kim C, et al. (2010) Non-cardiomyocytes influence the electrophysiological maturation of human embryonic stem cell-derived cardiomyocytes during differentiation. Stem Cells Dev. 19: 783-795.
Kim J, et al. (2002) Dopamine neurons derived from embryonic stem cells function in an animal model of Parkinson's disease. Nature. 418: 50-56.
Kim K, et al. (2011) Calibrated micropost arrays for biomechanical characterization of cardiomyocytes. Micro and Nano Letters. 6: 317-322.
Kim SU, et al. (2002) Production of immortalized human neural crest stem cells. Methods Mol Biol. 198: 55-65.
King T, et al. (2000) Piezoactuators for 'real-world' applications—Can they deliver sufficient displacement? Power Engineering. 14: 105-110.
Kingshott P and Griesser HJ. (1999) Surfaces that resist bioadhesion. Current Opinion in Solid State and Materials Science. 4: 403-412.
Kirazov E, et al. (2008) Amyloid beta peptides exhibit functional neurotoxicity to cortical network cultures. Compt Rend Acad Bulg Sci. 61: 905-910.
Kita-Matsuo H, et al. (2009) Lentiviral vectors and protocols for creation of stable hESC lines for fluorescent tracking and drug resistance selection of cardiomyocytes. PLoS One. 4: e5046.

(56) References Cited

OTHER PUBLICATIONS

Kleber AG and Rudy Y. (2004) Basic mechanisms of cardiac impulse propagation and associated arrhythmias. Physiol Rev. 84: 431-488.
Klein C, et al. (2002) Zinc inhibition of cAMP signaling. J Biol Chem. 277: 11859-11865.
Klein WL. (2002) Abeta toxicity in Alzheimer's disease: globular oligomers (ADDLs) as new vaccine and drug targets. Neurochem Int. 41: 345-352.
Kleinfeld D, et al. (1988) Controlled outgrowth of dissociated neurons on patterned substrates. J Neurosci. 8: 4098-4120.
Knobloch M and Mansuy IM. (2008) Dendritic spine loss and synaptic alterations in Alzheimer's disease. Mol Neurobiol. 37: 73-82.
Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.
Kobayashi T, et al. (1987) Human muscle cultured in monolayer and cocultured with fetal rat spinal cord: importance of dorsal root ganglia for achieving successful functional innervation. JNeurosci. 7: 3131-3141.
Koike T, et al. (2008) Axon & dendrite degeneration: its mechanisms and protective experimental paradigms. Neurochem Int. 52: 751-760.
Koirala S, et al. (2003) Roles of glial cells in the formation, function, and maintenance of the neuromuscular junction. J Neurocytol. 32: 987-1002.
Koleva M, et al. (2005) Pleiotropic effects of sonic hedgehog on muscle satellite cells. Cell Mol Life Sci. 62: 1863-1870.
Koliatsos VE, et al. (2008) Human stem cell grafts as therapies for motor neuron disease. Expert Opin Biol Ther. 8: 137-141.
Kontrogianni-Konstantopoulos A, et al. (2009) Muscle giants: molecular scaffolds in sarcomerogenesis. Physiol Rev. 89: 1217-1267.
Kornblum HI, et al. (1999) Multiple trophic actions of heparin-binding epidermal A511. growth factor (HB-EGF) in the central nervous system. Eur J Neurosci. 11: 3236-3246.
Kucera J and Dorovini-Zis K. (1979). Types of human intrafusal muscle fibers. Muscle Nerve. 2: 437-451.
Kucera J and Walro J. (1992) Axotomy induces fusimotor-free muscle spindles in neonatal rats. Neurosci Lett. 136: 216-218.
Kucera J, et al. (1989) Role of nerve and muscle factors in the development of rat muscle spindles. Am J Anat. 186: 144-160.
Kucera J. (1982a) One-bag-fiber muscle spindles in tenuissimus muscles of the cat. Histochemistry and Cell Biology. 76: 315-328.
Kucera, J. (1982b). The topography of long nuclear chain intrafusal fibers in the cat muscle spindle. Histochemistry. 74: 183-197.
Kucera, J. (1983). Multiple-bag-fiber muscle spindles in tenuissimus muscles of the cat. Histochemistry. 79: 457-476.
Kudla AJ, et al. (1995) A requirement for fibroblast growth factor in regulation of A518. skeletal muscle growth and differentiation cannot be replaced by activation of platelet-derived growth factor signaling pathways. Mol Cell Biol. 15: 3238-3246.
Kuhl U, et al. (1982) Synthesis of type IV collagen and laminin in cultures of skeletal muscle cells and their assembly on the surface of myotubes. Dev Biol. 93: 344-354.
Kuhl U, et al. (1986) Role of laminin and fibronectin in selecting myogenic versus fibrogenic cells from skeletal muscle cells in vitro. Dev Biol. 117: 628-635.
Kumar S, et al. (1998) NT-3-mediated TrkC receptor activation promotes proliferation and cell survival of rodent progenitor oligodendrocyte cells in vitro and in vivo. J Neurosci Res. 54: 754-765.
Kurek JB, et al. (1996) Leukemia inhibitory factor and interleukin-6 are produced by diseased and regenerating skeletal muscle. Muscle Nerve. 19: 1291-1301.

Lacor PN, et al. (2007) Abeta oligomer-induced aberrations m synapse composition, shape, and density provide a molecular basis for loss of connectivity in Alzheimer's disease. J Neurosci. 27: 796-807.
Lacor PN. (2007) Advances on the understanding of the origins of synaptic pathology in Ad. Curr Genomics. 8: 486-508.
Laflamme MA, et al. (2007) Cardiomyocytes derived from human embryonic stem cells in pro-survival factors enhance function of infarcted rat hearts. Nat Biotechnol. 25: 1015-1024.
Lamb TM, et al. (1993) Neural induction by the secreted polypeptide noggin. Science. 262: 713-718.
Lambert MP, et al. (1998) Diffusible, nonfibrillar ligands derived from Abeta1-42 are potent central nervous system neurotoxins. Proc Natl Acad Sci US A. 95:6448-6453.
Lambeth MJ and Kushmerick MJ. (2002) A computational model for glycogenolvsis in skeletal muscle. Ann Biomed Eng. 30: 808-827.
Lambrechts D, et al. (2003) VEGF is a modifier of amyotrophic lateral sclerosis in mice and humans and protects motoneurons against ischemic death. Nat Genet. 34: 383-394.
Langen RC, et al. (2003) Enhanced myogenic differentiation by extracellular matrix is regulated at the early stages of myogenesis. In Vitro Cell Dev Biol Anim. 39: 163-169.
Langer R and Vacanti JP. (1993) Tissue engineering. Science. 260: 920-926.
Larkin LM, et al. (2006) Functional evaluation of nerve-skeletal muscle constructs engineered in vitro. In Vitro Cell Dev Biol Anim. 42: 75-82.
Larsson L and Ansved T. (1995) Effects of ageing on the motor unit. Prog Neurobiol. 45: 397-415.
Lasser KE, et al. (2002) Timing of new black box warnings and withdrawals for prescription medications. JAMA. 287: 2215-2220.
Lawrence CL, et al. (2005) Nonclinical proarrhythmia models: predicting Torsades de Pointes. J Pharmacol Toxicol Methods. 52: 46-59.
Lawrence CL, et al. (2006) A rabbit Langendorff heart proarrhythmia model: predictive value for clinical identification of Torsades de Pointes. Br J Pharmacol. 149: 845-860.
Le Douarin NM and Dupin E. (2003) Multipotentiality of the neural crest. Curr Opin Genet Dev. 13: 529-536.
Lee A. (2005) Isolation of neural stem cells from the postnatal cerebellum. Nat Neurosci. 8: 723-729.
Lee EW, et al. (2003) Neuropeptide Y induces ischemic angiogenesis and restores function of ischemic skeletal muscles. J Clin Invest. 111: 1853-1862.
Lee G, et al. (2007) Isolation and directed differentiation of neural crest stem cells derived from human embryonic stem cells. Nat Biotechnol. 25: 1468-1475.
Lee G, et al. (2010) Derivation of neural crest cells from human pluripotent stem cells. Nat Protoc. 5: 688-701.
Lee HY, et al. (2004) Instructive role of Wnt/beta-catenin in sensory fate specification in neural crest stem cells. Science. 303: 1020-1023.
Lee MJ, et al. (2003) Hereditary sensory neuropathy is caused by a mutation in the delta subunit of the cytosolic chaperonin-containing t-complex peptide-I (Cct4) gene. Hum Mol Genet. 12: 1917-1925.
Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.
Lescaudron L, et al. (1999) Blood borne macrophages are essential for the triggering of muscle regeneration following muscle transplant. Neuromuscul Disord. 9: 72-80.
Levenberg S. et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation ofNMDA receptors by cyclin-dependent kinase-5 Proc Natl Acad Sci US A. 98: 12742-12747.

(56) References Cited

OTHER PUBLICATIONS

Li L and Olson EN. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropatterns. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4:e312.
Li XJ, et al. (2005) Specification of motoneurons from human embryonic stem cells. Nat Boltechnol. 23: 215-221.
Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. CurrNeurovasc Res. 3: 281-288.
Lin JW, et al. (2008) Region [corrected] of slowed conduction acts as core for spiral wave reentry in cardiac cell monolayers. Am J Physiol Heart Circ Physiol. 294: H58-H65.
Lin LF, et al. (1993) GDNF: a glial cell line-derived neurotrophic factor for midbrain dopaminergic neurons. Science. 260: 1130-1132.
Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: S173-S179.
Liu CN, et al. (2000) Spinal nerve injury enhances subthreshold membrane potential oscillations m DRG neurons: relation to neuropathic pam. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S, et al. (2000) Embryonic stem cells differentiate into oligodendrocytes and myelinate in culture and after spinal cord transplantation. Proc Natl Acad Sci USA. 97: 6126-6131.
Liu TX, et al. (2006) Blinded validation of the isolated arterially perfused rabbit ventricular wedge in preclinical assessment of drug-induced proarrhythmias. Heart Rhythm. 3: 948-956.
Liu WP, et al. (2005) Enantioselectivity in environmental safety of current chiral insecticides. Proc Natl Acad Sci US A. 102: 701-706.
Lochter AJ, et al. (1995) Control of neuronal morphology in vitro: interplay between adhesive substrate forces and molecular instruction. J Neurosci Res. 42:145-158.
Long C, et al. (2012) Design optimization of liquid-phase flow patterns for microfabricated lung on a chip. Ann Biomed Eng. 40: 1255-1267.
Lou XJ. (2009) Polarization fatigue in ferroelectric thin films and related materials. Journal of Applied Physics. 105: 024101-024124.
Love S. (2003) Neuronal expression of cell cycle-related proteins after brain ischaemia in man. Neurosci Lett. 353: 29-32.
Lu B, et al. (1996) Expression of synapsin I correlates with maturation of the neuromuscular synapse. Neuroscience. 74: 1087-1097.
Lu HR, et al. (2006) In-vitro experimental models for the risk assessment of antibiotic-induced QT prolongation. Eur J Pharmacol. 553: 229-239.
Ludwig T and A Thomson J. (2007) Defined, feeder-independent medium for human embryonic stem cell culture. Curr Protoc Stem Cell Biol. Chapter 1: Unit IC.2.
Lund AE and Narahashi T. (1982) Dose-dependent interaction of the pyrethroid isomers with sodium channels of squid axon membranes. Neurotoxicology. 3: 11-24.
Luo Y, et al. (2006) Effects of growth factors on extracellular matrix production by vocal fold fibroblasts in 3-dimensional culture. Tissue Eng. 12: 3365-3374.
Lyles JM, et al. (1992) Matrigel enhances myotube development in a serum-free defined medium. Intl Dev Neurosci. 10: 59-73.
Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.
Machida S, et al. (2004) Primary rat muscle progenitor cells have decreased proliferation and myotube formation during passages. Cell Prolif. 37: 267-277.
Maduell F. (2005) Hemodiafiltration. Hemodial Int. 9: 47-55.
Mahler GJ, et al. (2009a) Characterization of a gastrointestinal tract microscale cell culture analog used to predict drug toxicity. Biotechnol Bioeng. 104: 193-205.
Mahler GJ, et al. (2009b) Characterization of Caco-2 and HT29-MTX cocultures in an in vitro digestion/cell culture model used to predict iron bioavailability. J Nutr Biochem. 20: 494-50.
Malerba A, et al. (2009) Selection of multipotent cells and enhanced muscle reconstruction by myogenic macrophage-secreted factors. Exp Cell Res. 315:915-927.
Maim C, et al. (2004) Leukocytes, cytokines, growth factors and hormones in human skeletal muscle and blood after uphill or downhill running. J Physiol. 556:983-1000.
Malo N, et al. (2006) Statistical practice in high-throughput screening data analysis. Nat Biotechnol. 24: 167-175.
Marhl M, et al. (2000) Complex calcium oscillations and the role of mitochondria and cytosolic proteins. Biosystems. 57: 75-86.
Marona HRN, et al. (1999) Determination of sparfloxacin and its degradation products by HPLC-PDA. J Antimicrob Chemother. 44: 301-302.
Marques MJ and Neto HS. (1997) Ciliary neurotrophic factor stimulates in vivo myotube formation in mice. Neurosci Lett. 234: 43-46.
Mars T, et al. (2001) Differentiation of glial cells and motor neurons during the formation of neuromuscular junctions in cocultures of rat spinal cord explant and human muscle. J Comp Neurol. 438: 239-251.
Mars T, et al. (2003) Functional innervation of cultured human skeletal muscle proceeds by two modes with regard to agrin effects. Neuroscience. 118: 87-97.
Mars T. (2008) Effects of LIF on Neuromuscular Junction Formation in Co-Cultures of Rat Spinal Cord Explant and Human Muscle. Croatica Chimica Acta, 81(1): 177-182.
Martin-Caraballo M and Greer JJ. (2000) Development of potassium conductances in perinatal rat phrenic motoneurons. J Neurophysiol. 83: 3497-3508.
Martinou JC, et al. (1992) Cholinergic differentiation factor (CDF/LIF) promotes survival of isolated rat embryonic motoneurons in vitro. Neuron. 8: 737-744.
Masu Y, et al. (1993) Disruption of the CNTF gene results in motor neuron degeneration. Nature. 365: 27-32.
Matsakas A and Patel K. (2009) Skeletal muscle fibre plasticity in response to selected environmental and physiological stimuli. Histol Histopathol. 24: 611-629.
Matsuda T, et al. (1992) Two-dimensional cell manipulation technology. An artificial neural circuit based on surface microphotoprocessing. ASAIO J. 38:M243-M247.
Matthews PB. (1964) Muscle spindles and their motor control. Physiol Rev. 44:219-288.
Mattson MP, et al. (1992) Beta-Amyloid Peptides Destabilize Calcium Homeostasis and Render Human Cortical-Neurons Vulnerable to Excitotoxicity. J Neurosci. 12: 376-389.
Matzno S, et al. (2003) Evaluation of the synergistic adverse effects of concomitant therapy with statins and fibrates on rhabdomyolysis. J Pharm Pharmacol. 55: 795-802.
Maves L, et al. (2007) Pbx homeodomain proteins direct Myod activity to promote fast-muscle differentiation. Development. 134: 3371-3382.

(56) References Cited

OTHER PUBLICATIONS

Maynard EM. (2001) Visual prostheses. Annu Rev Biomed Eng. 3: 145-168.
McAuliffe GJ, et al. (2008) Development of a gastrointestinal tract microscale cell culture analog to predict drug transport. Mol Cell Biomech. 5:119-132.
McBeath R, et al. (2004) Cell shape, cytoskeletal tension, and RhoA regulate stem cell lineage commitment. Dev Cell. 6: 483-495.
McDevitt TC, et al. (2002) In vitro generation of differentiated cardiac myofibers on micropatterned laminin surfaces. J Biomed Mater Res. 60: 472-479.
McMahon JA, et al. (1998) Noggin-mediated antagonism of BMP signaling is required for growth and patterning of the neural tube and somite. Genes Dev. 12:1438-1452.
Megeney LA, et al. (1996) bFGF and LIF signaling activates STAT3 in proliferating myoblasts. Dev Genet. 19: 139-145.
Mehra S, et al. (2004) A boolean algorithm for reconstructing the structure of regulatory networks. Metab Eng. 6: 326-339.
Meijer L and Raymond E. (2003) Roscovitine and other purines as kinase inhibitors. From starfish oocytes to clinical trials. Ace Chem Res. 36: 417-425.
Melendez-Vasquez CV, et al. (2001) Nodes of Ranvier form in association with ezrin-radixin-moesin (ERM)-positive Schwann cell processes. Proc Natl Acad Sci US A. 98: 1235-1240.
Mendelsohn JD, et al. (2003) Rational design of cytophilic and cytophobic polyelectrolyte multilayer thin films. Biomacromolecules. 2003 4: 96-106.
Menendez L, et al. (2011) Wnt signaling and a Smad pathway blockade direct the differentiation of human pluripotent stem cells to multipotent neural crest cells. Proc Natl Acad Sci US A. 108: 19240-19245.
Menn B, et al. (2010) Delayed treatment with systemic (S)-roscovitine provides neuroprotection and inhibits in vivo CDK5 activity increase in animal stroke models. PLoS One. 5: e1211.
Metzger SW, et al. (1999) Development and characterization of surface chemistries for microfabricated biosensors. J of Vacuum Sci & Tech a—Vacuum Surfaces and Films. 17: 2623-2628.
Meyer G and Nabil MA. (1988) Novel optical approach to atomic force microscopy. Applied Physics Letters. 53: 1045-1047.
Meyer T, et al. (2004) Micro-electrode arrays in cardiac safety pharmacology—A novel tool to study QT interval prolongation. Drug Saf. 27: 763-772.
Meyer T, et al. (2004b) QT-screen: high-throughput cardiac safety pharmacology by extracellular electrophysiology on primary cardiac myocytes. Assay Drug Dev Technol. 2: 507-514.
Miles GB, et al. (2004) Functional properties of motoneurons derived from mouse embryonic stem cells. J Neurosci. 24: 7848-7858.
Miller FD. (2007) Riding the waves: neural and nonneural ongms for mesenchymal stem cells. Cell Stem Cell. 1: 129-130.
Miller SC, et al. (1988) Tumor necrosis factor inhibits human myogenesis in vitro. Mol Cell Biol. 8: 2295-2301.
Mitsumoto H, et al. (2001) Effects of cardiotrophin-1 (CT-1) in a mouse motor neuron disease. Muscle Nerve. 24: 769-777.
Mizuseki K, et al. (2003) Generation of neural crest-derived peripheral neurons and floor plate cells from mouse and primate embryonic stem cells. Proc Natl Acad Sci US A. 100: 5828-5833.
Moe GK. (1962) On the multiple wavelet hypothesis of atrial fibrillation. Arch Int Pharmacodyn Ther. 183-188.
Mohammed JS, et al. (2004) Micropatterning of nanoengineered surfaces to study neuronal cell attachment in vitro. Biomacromolecules. 5: 1745-1755.
Mohan DK, et al. (2006) Toxin detection based on action potential shape analysis using a realistic mathematical model of differentiated NG 108-15 cells. Biosens Bioelectron. 21: 1804-1811.
Mokry J, et al. (2007) Differentiation of neural stem cells into cells of oligodendroglial lineage. Acta Medica (Hradec Kralove). 50: 35-41.

Molnar P, et al. (2007) Photolithographic Patterning of C2C12 Myotubes using Vitronectin as Growth Substrate in Serum-Free Medium. Biotechnol Prog. 23:265-268.
Molnar P, et al. (2007b) Synaptic connectivity in engineered neuronal networks. Methods Mol Biol. 403: 165-173.
Molnar P, et al. (2007c) Modeling of action potential generation in NG 108-15 cells. Methods Mol Biol. 403: 175-184.
Monaco EA 3rd and Vallano ML. (2005) Roscovitine triggers excitotoxicity in cultured granule neurons by enhancing glutamate release. Mol Pharmacol. 68:1331-1342.
Monaco EA 3rd. (2004) Recent evidence regarding a role for Cdk5 dysregulation in Alzheimer's disease. Curr Alzheimer Res. 1: 33-38.
Monyer H, et al. (1994) Developmental and regional expression in the rat brain and functional properties of four NMDA receptors. Neuron. 12: 529-540.
Moore JW, et al. (1991) The mRNAs encoding acidic FGF, basic FGF and FGF receptor are coordinately downregulated during myogemc differentiation. Development. 111: 741-748.
Morefield SI, et al. (2000) Drug evaluations using neuronal networks cultured on microelectrode arrays. Biosens Bioelectron. 15: 383-396.
Morimoto S, et al. (1984) Dependence of conduction velocity on spike interval during voluntary muscular contraction in human motor units. Eur J Appl Physiol Occup Physiol. 53(3):191-195.
Morin F, et al. (2006) Constraining the connectivity of neuronal networks cultured on microelectrode arrays with microfluidic techniques: a step towards neuron-based functional chips. Biosens Bioelectron. 21: 1093-1100.
Morrow NG, et al. (1990) Increased expression of fibroblast growth factors in a rabbit skeletal muscle model of exercise conditioning. J Clin Invest. 85: 1816-1820.
Motamed K, et al. (2003) Fibroblast growth factor receptor-I mediates the inhibition of endothelial cell proliferation and the promotion of skeletal myoblast differentiation by SPARC: a role for protein kinase A. J Cell Biochem. 90: 408-423.
Moulard G, et al. (1998) Improvement of the cantilever beam technique for stress measurement during the physical vapor deposition process. J Vac Science Technol A. 16(2): 736-742.
Mousavi K, et al. (2004) BDNF rescues myosin heavy chain IIB muscle fibers after neonatal nerve injury. Am J Physiol Cell Physiol. 287: C22-C29.
Mrksich M. (2000) A surface chemistry approach to studying cell adhesion. Biosensors & Bioelectronics. 29: 267-273.
Mufti NA and Shuler ML. (1998) Different In Vitro Systems Affect CYPIAI Activity in Response to 2,3,7,8-Tetrachlorodibenzo-p-dioxin. Toxicol In Vitro. 12: 259-272.
Mulkey D, et al. (2003) Hyperbaric oxygen and chemical oxidants stimulate $CO_2/H+$-sensitive neurons in rat brain stem slices. J Appl Physiol. 95: 910-92.
Mullen RJ, et al. (1992) NeuN, a neuronal specific nuclear protein in vertebrates. Development. 116: 201-211.
Muller FJ, et al. (2006) Gene therapy: can neural stem cells deliver? Nat Rev Neurosci. 7: 75-84.
Muller P and Saul A. (2004) Elastic effects on surface physics. Surface Science Reports. 54: 157-258.
Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.
Muraki K, et al. (1994) Effects of noradrenaline on membrane currents and action potential shape in smooth muscle cells from guinea-pig ureter. J Physiol. 481:617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.

(56) References Cited

OTHER PUBLICATIONS

Mutyala MSK, et al. (2009) Mechanical and electronic approaches to improve the sensitivity ofmicrocantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan to Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.
Nam Y, et al. (2006) Neural recording and stimulation of dissociated hippocampal cultures using microfabricated three-dimensional tip electrode array. J Neurosci Methods. 155: 296-299.
Nash MP, et al. (2004) Electromechanical model of excitable tissue to study reentrant cardiac arrhythmias. Prog Biophys Mol Biol. 85(2-3):501-522.
Nash MP, et al. (2006) Evidence for multiple mechanisms in human ventricular fibrillation. Circulation. 114: 536-542.
Nat R. (2011) Cortical network from human embryonic stem cells. J Cell Mol Med. 15: 1429-1431.
Natarajan A, et al. (2006) Microelectrode array recordings of cardiac action potentials as a high throughput method to evaluate pesticide toxicity. Toxicol In Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32:4267-4274.
Natarajan A, et al. (2013) Engineered In Vitro Feed-Forward Networks. J Biotechnol Biomater. 3:153.
Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.
Nelson CM and Bisell MJ. (2006) Of extracellular matrix, scaffolds, and signaling: tissue architecture regulates development, homeostasis, and cancer. Annu Rev Cell Dev Biol. 22: 287-309.
Nelson PG, et al. (1993) Synapse elimination from the mouse neuromuscular junction in vitro: a non-Hebbian activity-dependent process. J Neurobiol. 24:1517-1530.
Nelson PG. (1975) Nerve and muscle cells in culture. Physiol Rev. 55: 1-61.
Nerbonne JM and Kass RS. (2005) Molecular physiology of cardiac repolarization. Physiol Rev. 85: 1205-1253.
Nguemo F, et al. (2012) In vitro model for assessing arrhythmogenic properties of drugs based on high-resolution impedance measurements. Cell Physiol Biochem. 29: 819-832.
Nguyen L, et al. (2006) The Yin and Yang of cell cycle progression and differentiation in the oligodendroglial lineage. Ment Retard Dev Disabil Res Rev. 12: 85-96.
Nicolelis MAL and Ribeiro S. (2002) Multielectrode recordings: the next steps. Curr Opin Neurobiol. 12: 602-606.
Nimmrich V, et al. (2008) Amyloid beta oligomers (A beta(I-42) globulomer) suppress spontaneous synaptic activity by inhibition of P/Q-type calcium currents. J Neurosci. 28: 788-797.
Nishikawa J, et al. (2005) Increase of Cardiotrophin-1 immunoreactivity in regenerating and overloaded but not denervated muscles of rats. Neuropathology. 25: 54-65.
Nishimaru H, et al. (2005) Mammalian motor neurons corelease glutamate and acetylcholine at central synapses. Proc Natl Acad Sci US A. 102: 5245-5249.

Nistor GI, et al. (2005) Human embryonic stem cells differentiate into oligodendrocytes in high purity and myelinate after spinal cord transplantation. Glia. 49: 385-396.
Noble D. (2004) Modeling the heart. Physiology (Bethesda). 19: 191-197.
Noll E and Miller RH. (1993) Oligodendrocyte precursors originate at the ventral ventricular zone dorsal to the ventral midline region in the embryonic rat spinal cord. Development. 118: 563-573.
Normann RA, et al. (1999) A neural interface for a cortical vision prosthesis. Vision Res. 39: 2577-2587.
Norris W, et al. (2000) Slow muscle induction by Hedgehog signalling in vitro. J Cell Sci. 113: 2695-2703.
Nugaeva N, et al. (2005) Micromechanical cantilever array sensors for selective fungal immobilization and fast growth detection. Biosens Bioelectron. 21(6):849-856.
Nyitrai G, et al. (2006) Extracellular level of GABA and Glu: III VIVO microdialysis-HPLC measurements. Curr Top Med Chem. 6: 935-940.
Oakley RA, et al. (1997) Neurotrophin-3 promotes the differentiation of muscle spindle afferents in the absence of peripheral targets. J Neurosci. 17: 4262-4274.
O'Connor SM, et al. (2000) Immobilization of neural cells in three-dimensional matrices for biosensor applications. Biosens Bioelectron. 14: 871-881.
Offenhausser A and Knoll W. (2001) Cell-transistor hybrid systems and their potential applications. Trends Biotechnol. 19: 62-66.
Offenhausser A, et al. (1997) Field-effect transistor array for monitoring electrical activity from mammalian neurons in culture. Biosensors and Bioelectronics. 12: 819-826.
Oh TI, et al. (2007) Real-time fluorescence detection of multiple microscale cell culture analog devices in situ. Cytometry A. 71: 857-865.
Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.
Olson E. (1992a) Activation of muscle-specific transcription by myogenic helixloop-helix proteins. Symp Soc Exp Biol. 46: 331-341.
Olson EN and Perry WM. (1992b) MyoD and the paradoxes of myogenesis. Curr Biol. 2: 35-37.
Olson EN and Williams RS. (2000) Calcineurin Signaling and Muscle Remodeling. Cell. 101: 689-692.
Olson EN. (1992c) Interplay between proliferation and differentiation within the myogenic lineage. Dev Biol. 154: 261-272.
Olwin BB and Rapraeger A. (1992) Repression of myogenic differentiation by aFGF, bFGF, and K-FGF is dependent on cellular heparan sulfate. J Cell Biol. 118: 631-639.
Oppenheim RW, et al. (1991) Control of embryonic motoneuron survival in vivo by ciliary neurotrophic factor. Science. 251: 1616-1618.
Oppenheim RW, et al. (2001) Cardiotrophin-1, a muscle-derived cytokine, is required for the survival of subpopulations of developing motoneurons. J Neurosci. 21: 1283-1291.
Orentas DM and Miller RH. (1998) Regulation of oligodendrocyte development. Mol Neurobiol. 18: 247-259.
Orlov SN and Hamet P. (2006) Intracellular monovalent ions as second messengers. J Membr Biol. 210: 161-172.
Ostuni E, et al. (2000) Patterning mammalian cells using elastomeric membranes. Langmuir. 16: 7811-7819.
Oumata N, et al. (2008) Roscovitine-derived, dual-specificity inhibitors of cyclindependent kinases and casein kinases 1. J Med Chem. 51: 5229-5242.
Padmanabhan J, et al. (1999) Role of cell cycle regulatory proteins in cerebellar granule neuron apoptosis. J Neurosci. 19: 8747-8756.
Pagan SM, et al. (1996) Surgical removal of limb bud Sonic hedgehog results in posterior skeletal defects. Dev Biol. 180: 35-40.
Pancrazio JJ, et al. (1998) Portable cell-based biosensor system for toxin detection. Sensors and Actuators B Chem. 53: 179-185.
Park J, et al. (2005) Real-time measurement of the contractile forces of self-organized cardiomyocytes on hybrid biopolymer microcantilevers. Anal Chem. 77: 6571-6580.

(56) References Cited

OTHER PUBLICATIONS

Parker KK, et al. (2008) Myofibrillar architecture m engineered cardiac myocytes. Circ Res. 103: 340-342.
Parng C, et al. (2002) Zebrafish: A Preclinical Model for Drug Screening. Assay Drug Dev Technol. 1: 41-48.
Parviz M and Gross GW. (2007) Quantification of zinc toxicity using neuronal networks on microelectrode arrays. Neurotoxicolo12:v. 28: 520-531.
Paspalas CD and Papadopoulos GC. (1996) Ultrastructural relationships between noradrenergic nerve fibers and non-neuronal elements in the rat cerebral cortex. Glia. 17: 133-146.
Payne ET, et al. (2006) Nutritional therapy improves function and complements corticosteroid intervention in mdx mice. Muscle Nerve. 33: 66-77.
Peng HB, et al. (2003) Differential effects of neurotrophins and schwann cell-derived signals on neuronal survival/growth and synaptogenesis. J Neurosci. 23:5050-5060.
Peroulakis ME and Forger NG. (2000) Ciliary neurotrophic factor increases muscle fiber number in the developing levator ani muscle of female rats. Neurosci Lett. 296: 73-76.
Perrier AL, et al. (2004) Derivation of midbrain dopamine neurons from human embryonic stem cells. Proc Natl Acad Sci USA. 101: 12543-12548.
Peters A. (1964) Observations on the Connexions Between A709. Myelin Sheaths and Glial Cells in the Optic Nerves of Young Rats. J Anat. 98: 125-134.
Peterson CA, et al. (1999) Effects of moisture on Fowler—Nordheim characterization of thin silicon-oxide films. J Vac Science Technol A. 17: 2753-2758.
Pette D and Staron S. (2001) Transitions of muscle fiber phenotypic profiles. Histochem and Cell Biol. 115: 359-372.
Pette D, et al. (2002) Partial fast-to-slow conversion of regenerating rat fast-twithc muscle by chronic low frequency stimulation. J Muscle Res Cell Motil. 3:215-221.
Pfeiffer SE, et al. (1993) The oligodendrocyte and its many cellular processes. Trends Cell Biol. 3: 191-197.
Pfrieger FW and Barres BA. (1997) Synaptic efficacy enhanced by glial cells in vitro. Science. 277: 1684-1687.
Pijnappels DA, et al. (2007) Resynchronization of separated rat cardiomyocyte fields with genetically modified human ventricular scar fibroblasts. Circulation. 116: 2018-2028.
Pillekamp F, et al. (2012) Contractile properties of early human embryonic stem cell-derived cardiomyocytes: beta-adrenergic stimulation induces positive chronotropy and lusitropy but not inotronv. Stem Cells Dev. 21: 2111-2121.
Podratz J, et al. (2004) Antioxidants are necessary for myelination of dorsal root ganglion neurons, in vitro. Glia. 45: 54-58.
Pomp O, et al. (2005) Generation of peripheral sensory and sympathetic neurons and neural crest cells from human embryonic stem cells. Stem Cells. 23: 923-930.
Pomp O, et al. (2008) PA6-induced human embryonic stem cell-derived neurospheres: a new source of human peripheral sensory neurons and neural crest cells. Brain Res. 1230: 50-60.
Pontier C, et al. (2001) HT29-MTX and Caco-2/TC7 monolayers as predictive models for human intestinal absorption: role of the mucus layer. J Pharm Sci. 90:1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.

Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.
Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and McMorris FA. (1989) Cyclic AMP regulates the rate of differentiation of oligodendrocytes without changing the lineage commitment of their progenitors. Dev Biol. 133: 437-446.
Raible DW and Mc Morris FA. (1990) Induction of oligodendrocyte differentiation by activators of adenylate cyclase. J Neurosci Res. 27: 43-46.
Raiteri R, et al. (2001) Micromechanical cantilever-based biosensors. Sensors and Actuators B—Chemical. 79: 115-126.
Rajnicek AM, et al. (1997) Contact guidance of CNS neurites on grooved quartz: influence of groove dimensions, neuronal age and cell type. J Cell Sci. 110: 2905-2913.
Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel HERG. FEBS Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K(+) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cell-derived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly( ethylene glycol) Photolithography to Create High-Density Cell Arrays on Glass. Langmuir. 19:9855-9862.
Reyes D, et al. (2004) Micropatterning neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.
Richert L, et al. (2004) pH dependent growth of poly(L-lysine )/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation m apolipoprotein E deficient and human apolipoprotein E transgenic mice. Neuroscience. 98: 353-359.
Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.

(56) References Cited

OTHER PUBLICATIONS

Rosenberg SS, et al. (2008) The geometric and spatial constraints of the microenvironment induce oligodendrocyte differentiation. Proc Natl Acad Sci USA. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1-beta-I. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. (1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. JNeurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-64.
Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-11.
Scherer J, et al. (1995) Differentiation and maturation of rabbit retinal oligodendrocyte precursor cells in vitro. Brain Res Dev Brain Res. 89: 214-226.
Schiaffino S and Serrano A. (2002) Calcineurin signaling and neural control of skeletal muscle fiber type and size. Trends Pharmacol Sci. 23: 569-575.
Schiaffino S, et al. (2007) Activity-Dependent Signaling Pathways Controlling Muscle Diversity and Plasticity. Physiology. 22: 269-278.
Schluter H and Kaur P. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276:C900-C906.
Scholzen T and Gerdes J. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, et al. (2005) Why drugs fail—a study on side effects in new chemical entities. Curr Pharm Des. 11: 3545-3559.
Schuster R and Holzhutter HG. (1995) Use of mathematical models for predicting the metabolic effect of large-scale enzyme activity alterations. Application to enzyme deficiencies ofred blood cells. Eur J Biochem. 229: 403-418.
Schwab ME. (2002) Repairing the injured spinal cord. Science. 295: 1029-1031.
Schwarz A, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote Mand Williams AJ. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KA TP channels integrated with creatine and adenylate kinases: amplification, tuning and sensing of energetic signals in the compartmentalized cellular environment. Mol Cell Biochem. 256-257: 243-256.
Selivanova OM, et al. (2003) Compact globular structure of Thermus thermophilus ribosomal protein S 1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006a) Paracrine release of insulin-like growth factor 1 from a bioengineered tissue stimulates skeletal muscle growth in vitro. Tissue Eng. 12:1833-1841.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.
Sheng Z, et al. (1996) Cardiotrophin-1 displays early expression in the murine heart tube and promotes cardiac myocyte survival. Development. 122: 419-428.
Sheridan DC, et al. (2003) Ca2+-dependent excitation-contraction coupling triggered by the heterologous cardiac/brain DHPR beta2a-subunit in skeletal myotubes. Biophys J. 85: 3739-3757.
Sheridan DC, et al. (2003) Truncation of the carboxyl terminus of the dihydropyridine receptor betaIa subunit promotes Ca2+ dependent excitation-contraction coupling in skeletal myotubes. Biophys J. 84: 220-237.
Sherman DL and Brophy PJ. (2005) Mechanisms of axon ensheathment and myelin growth. Nat Rev Neurosci. 6: 683-690.
Sherman DL, et al. (2005) Neurofascins are required to establish axonal domains for saltatory conduction. Neuron. 48: 737-742.
Shimono K, et al. (2000) Multielectrode Recording of Rhythmic Oscillations in Brain Slices: A Novel Technique for Screening Psychoactive Drugs. Faseb J. 14:1047.
Shin S, et al. (2005) Human motor neuron differentiation from human embryonic stem cells. Stem Cells Dev. 14: 266-269.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.

(56) References Cited

OTHER PUBLICATIONS

Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19:317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith J and Schofield PN. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313:107-1.
Smith PF, et al. (1991) HMG-CoA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. ACS Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.
Soundarapandian MM, et al. (2007) Role of K(ATP) channels in protection against neuronal excitatory insults. J Neurochem. 103: 1721-172.
Soundararajan P, et al. (2007) Easy and rapid differentiation of embryonic stem cells into functional motoneurons using sonic hedgehog-producing cells. Stem Cells. 25: 1697-1706.
Spach MS and Heidlage JF. (1995) The stochastic nature of cardiac propagation at a microscopic level. Electrical description of myocardial architecture and its application to conduction. Circ Res. 76: 366-380.
Spach MS. (1983) The role of cell-to-cell coupling in cardiac conduction disturbances. Adv Exp Med Biol. 161: 61-77.
Spargo BJ, et al. (1994) Spatially controlled adhesion, spreading, and differentiation of endothelial cells on self-assembled molecular monolayers. Proc Natl Acad Sci USA. 91: 11070-11074.
Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.
St John PM, et al. (1997) Preferential glial cell attachment to microcontact printed surfaces. J Neurosci Methods. 75: 171-177.
St. George-Hyslop PH and Petit A. (2005) Molecular biology and genetics of Alzheimer's disease.CR Biol. 328: 119-130.
Stavarachi M, et al. (2010) Spinal muscular atrophy disease: a literature review for therapeutic strategies. J Med Life. 3: 3-9.
Steffen LS, et al. (2007) Zebrafish orthologs of human muscular dystrophy genes. BMC Genomics. 8: 7.
Stenger DA, et al. (1992) Coplanar Molecular Assemblies of Aminoalkylsilane and Perfluorinated Alkylsilane—Characterization and Geometric Definition of Mammalian-Cell Adhesion and Growth. Journal of the American Chemical Society. 114: 8435-8442.
Stenger DA, et al. (1993) Surface determinants of neuronal survival and growth on self-assembled monolayers in culture. Brain Res. 630: 136-147.
Stenger DA, et al. (1998) Microlithographic determination of axonal/dendritic polarity in cultured hippocampal neurons. J Neurosci Methods. 82: 167-173.
Sternberger NH, et al. (1985) Immunocytochemistry of myelin basic proteins in adult rat oligodendroglia. J Neuroimmunol. 7: 355-363.
Stett A, et al. (2003) Biological application of microelectrode arrays in drug discovery and basic research. Anal Bioanal Chem. 377: 486-495.
Stevens JL. (2006) Future of toxicology—mechanisms of toxicity and drug safety: where do we go from here? Chem Res Toxicol. 19: 1393-1401.
Stinstra J, et al. (2006) A Model of 3D Propagation in Discrete Cardiac Tissue. Comput Cardiol. 33: 41-44.
Stockwell BR. (2004) Exploring biology with small organic molecules. Nature. 432: 846-854.
Stoney GG. (1909) The Tension of Metallic Films Deposited by Electrolysis. Proc Roy Soc London. 82: 172-175.
Subramanian B, et al. (2010) Tissue-engineered three-dimensional in vitro models for normal and diseased kidney. Tissue Eng Part A. 16: 2821-2831.
Sun L, et al. (2007) JAK1-STAT1-STAT3, a key pathway promoting proliferation and preventing premature differentiation of myoblasts. J Cell Biol. 179: 129-138.
Sung JH and Shuler ML. (2009a) A micro cell culture analog (microCCA) with 3-D hydrogel culture of multiple cell lines to assess metabolism-dependent cytotoxicity of anti-cancer drugs. Lab Chip. 9: 1385-1394.
Sung JH and Shuler ML. (2009b) Prevention of air bubble formation in a microfluidic perfusion cell culture system using a microscale bubble trap. Biomed Microdevices. 11: 731-738.
Sung JH, et al. (2009c) Fluorescence optical detection in situ for real-time monitoring of cytochrome P450 enzymatic activity of liver cells in multiple microfluidic devices. Biotechnol Bioeng. 104: 516-525.
Sung JH, et al. (2010) A microfluidic device for a pharmacokinetic-pharmacodynamic (PK-PD) model on a chip. Lab Chip. 10: 446-455.
Sung JH, et al. (2013) Microfabricated mammalian organ systems and their integration into models of whole animals and humans. Lab Chip. 13: 1201-1212.
Suter W. (2006) Predictive value of in vitro safety studies. Curr Opin Chem Biol. 10: 362-366.
Sutton NM, et al. (2007) Clinical effects and outcome of feline permethrin spot-on poisonings reported to the Veterinary Poisons Information Service (VPIS), London. J Feline Med Surg. 9: 335-339.
Swasdison Sand Mayne R. (1992) Formation of highly organized skeletal muscle fibers in vitro. Comparison with muscle development in vivo. J Cell Sci. 102:643-652.
Swynghedauw B. (1999) Molecular mechanisms of myocardial remodeling. Physiol Rev. 79: 215-262.
Takagishi Y, et al. (2000) Species-specific difference in distribution of voltage-gated L-type Ca(2+) channels of cardiac myocytes. Am J Physiol Cell Physiol. 279: C1963-C1969.
Takahashi T. (1978) Intracellular recording from visually identified motoneurons in rat spinal cord slices. Proc R Soc Lond B Biol Sci. 202: 417-421.
Takashima Y, et al. (2007) Neuroepithelial cells supply an initial transient wave of MSC differentiation. Cell. 129: 1377-1388.
Tan W and Desai TA. (2003) Microfluidic patterning of cells in extracellular matrix biopolymers: effects of channel size, cell type, and matrix composition on pattern integrity. Tissue Eng. 9: 255-267.
Tanaka M, et al. (2005) An Unbiased Cell Morphology Based Screen for New, Biologically Active Small Molecules. PLoS Biol. 3: e128.

(56) References Cited

OTHER PUBLICATIONS

Tanaka Y, et al. (2006) An actuated pump on-chip powered by cultured cardiomyocytes. Lab Chip. 6: 362-368.
Tarasenko YI, et al. (2007) Human fetal neural stem cells grafted into contusion-injured rat spinal cords improve behavior. JN eurosci Res. 85: 4 7-57.
Tatosian DA and Shuler ML. (2009) A novel system for evaluation of drug mixtures for potential efficacy in treating multidrug resistant cancers. Biotechnol Bioeng. 103: 187-198.
Termin A and Pette D. (1992) Changes in myosin heavy-chain isoform synthesis of chronically stimulated rat fast-twitch muscle. Eur J Biochem. 204: 569-573.
Terstappen GC, et al. (2007) Target deconvolution strategies in drug discovery. Nat. Rev Drug Discov. 6: 891-9.
Thomas CA, et al. (1972) A miniature microelectrode array to monitor the bioelectric activity of cultured cells. Exp Cell Res. 74: 61-66.
Thomas R. (1973) Boolean formalization of genetic control circuits. J Theor Biol. 1973. 42: 563-585.
Thompson PD, et al. (2006) An assessment of statin safety by muscle experts. Am J Cardiol. 97: 69C-76C.
Thompson RB, et al. (2005) Intracardiac transplantation of a mixed population of bone marrow cells improves both regional systolic contractility and diastolic relaxation. J Heart Lung Transplant. 24: 205-214.
Thorrez L, et al. (2008) Growth, differentiation, transplantation and survival of human skeletal myofibers on biodegradable scaffolds. Biomaterials. 29: 75-84.
Timmerman W and Westerink BH. (1997) Brain microdialysis of GABA and glutamate: what does it signify? Synapse. 27: 242-261.
Tobert JA. (2003) Lovastatin and beyond: the history of the HMGCoA reductase inhibitors. Nat Rev Drug Discov. 2: 517-526.
Toga T, et al. (2007) The 5-HT( 4) agonists cisapride, mosapride, and CJ-033466, a Novel potent compound, exhibit different human ether-a-go-go-related gene (hERG)-blocking activities. J Pharmacol Sci. 105: 207-210.
Tomb JF, et al. (1997) The complete genome sequence of the gastric pathogen Helicobacter pylori. Nature. 388: 539-547.
Torgan CE and Daniels MP. (2001) Regulation of myosin heavy chain expression during rat skeletal muscle development in vitro. Mol Biol Cell. 12: 1499-1508.
Torgan CE and Daniels MP. (2006) Calcineurin localization in skeletal muscle offers insights into potential new targets. J Histochem Cytochem. 54: 119-128.
Torimitsu Kand Kawana A. (1990) Selective growth of sensory nerve fibers on metal oxide pattern in culture. Brain Res Dev Brain Res. 51: 128-131.
Townsend KP and Pratico D. (2005) Novel therapeutic opportunities for Alzheimer's disease: focus on nonsteroidal anti-inflammatory drugs. FASEB J.
Tung L and Cysyk J. (2007) Imaging fibrillation/defibrillation in a dish. J Electrocardiol. 40: S62-S65.
Tung L and Zhang YB. (2006) Optical imaging of arrhythmias in tissue culture. J Electrocardiol. 39: S2-S6.
Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.
Umbach JA, et al. (2012) Functional neuromuscular junctions formed by embryonic stem cell-derived motor neurons. PLoS One. 7: e36049.
Urakami H and Chiu A Y. (1990) A monoclonal antibody that recognizes somatic motor neurons in the mature rat nervous system. J Neurosci. 10: 620-630.
Urazaev AK, et al. (1995) Muscle NMDA receptors regulate the resting membrane potential through NO-synthase. Physiol Res. 44: 205-20.
Vakakis N, et al. (1995) In vitro myoblast to myotube transformations in the presence ofleukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacol Toxicol Methods. 49: 171-181.
van de Ven C, et al. (2007) The potential of umbilical cord blood multipotent stem cells for nonhematopoietic tissue and cell regeneration. Exp Hematol. 35:1753-1765.
van der Valk J, et al. (2010) Optimization of chemically defined cell culture media—replacing fetal bovine serum in mammalian in vitro methods. Toxicol In Vitro. 24: 1053-1063.
van Rijen HV, et al. (2006) Connexins and cardiac arrhythmias. Adv Cardiol. 42:150-160.
van Soest PF and Kits KS. (1998) Conopressin affects excitability, firing, and action potential shape through stimulation of transient and persistent inward currents in mulluscan neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.
Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue A888. culture: Effects on skeletal muscle organogenesis. In Vitro Cell Dev Biol. 24:609-619.
Varghese K, et al. (2009) Regeneration and characterization of adult mouse A889. hippocampal neurons in a defined in vitro system. J N eurosci Methods. 177: 51-59.
Varghese K, et al. (2010) A new target for amyloid beta toxicity validated by standard and high-throughput electrophysiologv. PLoS One. 5: e8643.
Vargo TG, et al. (1992) Monolayer Chemical Lithography and Characterization of Fluoropolymer Films. Langmuir. 8: 130-1.
Vartanian T, et al. (1988) Oligodendrocyte substratum adhesion modulates expression of adenylate cyclase-linked receptors. Proc Natl Acad Sci US A. 85:939-943.
Ventimiglia R, et a. (1987) Localization of beta-adrenergic receptors on differentiated cells of the central nervous system in culture. Proc Natl Acad Sci USA. 84: 5073-507.
Vidarsson H, et al. (2010) Differentiation of human embryonic stem cells to cardiomyocytes for in vitro and in vivo applications. Stem Cell Rev. 6: 108-120.
Viravaidya K and Shuler ML. (2004) Incorporation of 3T3-LI cells to mimic bioaccumulation in a microscale cell culture analog device for toxicity studies. Biotechnol Prog. 20: 590-597.
Vogel V and Sheetz M. (2006) Local force and geometry sensing regulate cell functions. Nat Rev Mol Cell Biol. 7: 265-275.
Vogel Z and Daniels MP. (1976) Ultrastructure of acetylcholine receptor clusters on cultured muscle fibers. J Cell Biol. 69: 501-507.
Waataja JJ, et al. (2008) Excitotoxic loss of post-synaptic sites is distinct temporally and mechanistically from neuronal death. J Neurochem. 104: 364-375.
Waggoner PS and Craighead HG. (2007) Micro- and nanomechanical sensors for environmental, chemical, and biological detection. Lab Chip. 7: 1238-1255.
Wagner I, et al. (2013) A dynamic multi-organ-chip for long-term cultivation and substance testing proven by 3D human liver and skin tissue co-culture. Lab Chip. 13: 3538-3547.
Wakatsuki T, et al. (2004) Phenotypic screening for pharmaceuticals using tissue constructs. Curr Pharm Biotechnol. 5: 181-189.
Walro JM and Kucera J. (1999) Why adult mammalian intrafusal and extrafusal fibers contain different myosin heavy-chain isoforms. Trends Neurosci. 22: 180-184.

(56) References Cited

OTHER PUBLICATIONS

Walsh DM and Selkoe DJ. (2007) A beta oligomers—a decade of discovery. J N eurochem. 101: 1172-1184.
Walsh K, et al. (2005) Human central nervous system tissue culture: a historical review and examination of recent advances. Neurobiol Dis. 18: 2-18.
Wang HW, et al. (2002) Soluble oligomers of beta amyloid (1-42) inhibit long-term potentiation but not long-term depression in rat dentate gyrus. Brain Res. 924: 133-140.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and A907. ciliary neurotrophic factor on the proliferation and differentiation of adult human myoblasts. Cell Mol Neurobiol. 28: 113-124.
Ward JH, et al. (2001) Micropatterning of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1 alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacol. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI—Nanotech. 2: 297-300.
Wilson K, et al. (2007) Integration of Functional Myotubes with a Bio-MEMS Device for Non-Invasive Interrogation. Lab Chip. 7: 920-922.
Wilson K, et al. (2010) Measurement of contractile stress generated by cultured rat muscle on silicon cantilevers for toxin detection and muscle performance enhancement. PLoS One. 5: e11042.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.
Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122:R43-R50.
Winslow RL, et al. (2005) Using models of the myocyte for functional interpretation of cardiac proteomic data. J Physiol. 563: 73-81.
Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation of myelination by Schwann cells. Ann NY Acad Sci. 605: 1-14.
Wright CD, et al. (2008) Nuclear alpha1-adrenergic receptors signal activated ERK localization to caveolae in adult cardiac myocytes. Circ Res. 103: 992-1000.
Wu H, et al. (2010) To build a synapse: signaling pathways in neuromuscular junction assembly. Development. 137: 1017-1033.
Wu P, et al. (2002) Region-specific generation of cholinergic neurons from fetal human neural stem cells grafted in adult rat. Nat Neurosci. 5: 1271-1278.
Wu ZR, et al. (2007) Layer-by-layer assembly of polyelectrolyte films improving cytocompatibility to neural cells. J Biomed Mater Res A. 81: 355-362.
Wyart C, et al. (2002) Constrained synaptic connectivity m functional mammalian neuronal networks grown on patterned surfaces. J Neurosci Methods. 117: 123-131.
Xi J, et al. (2005) Self-assembled microdevices driven by muscle. Nat Mater. 4:180-184.
Xu C, et al. (2006) Growth and differentiation of human embryonic stem cells for cardiac cell replacement therapy. Curr Stem Cell Res Ther. 1: 173-187.
Xu H, et al. (2008) Development of a stable dual cell-line GFP expression system to study estrogenic endocrine disruptors. Biotechnol Bioeng. 101: 1276-1287.
Xu L, et al. (2006) Human neural stem cell grafts ameliorate motor neuron disease in SOD-I transgenic rats. Transplantation. 82: 865-875.
Xu T, et al. (2004) Construction of high-density bacterial colony arrays and patterns by the ink-jet method. Biotechnol Bioeng. 85: 29-33.
Xu T, et al. (2005) Inkjet printing of viable mammalian cells. Biomaterials. 26:93-99.
Xu T, et al. (2006) Viability and electrophysiology of neural cell structures generated by the inkjet printing method. Biomaterials. 27: 3580-3588.
Xu T, et al. (2009) Electrophysiological characterization of embryonic hippocampal neurons cultured in a 3D collagen hydrogel. Biomaterials. 30: 4377-4383.
Yablonka-Reuveni Z. (1995) Development and postnatal regulation of adult myoblasts. Microsc Res Tech. 30: 366-380.
Yan J, et al. (2007) Extensive neuronal differentiation of human neural stem cell grafts in adult rat spinal cord. PLoS Med. 4: 318-33.
Yan Z, et al. (2002) Roscovitine: a novel regulator of P/Q-type calcium channels and transmitter release in central neurons. J Physiol. 540: 761-770.
Yang FS, et al. (2005) Curcumin inhibits formation of amyloid beta oligomers and fibrils, binds plaques, and reduces amyloid in vivo. J Biol Chem. 280: 5892-5901.
Yang J, et al. (2006) Synthesis and evaluation of poly( diol citrate) biodegradable elastomers. Biomaterials. 27: 1889-1898.
Yang L, et al. (2007) Increased asynchronous release and aberrant calcium channel activation m amyloid precursor protein deficient neuromuscular synapses. Neuroscience. 149: 768-778.
Yang LX and Nelson PG. (2004) Glia cell line-derived neurotrophic factor regulates the distribution of acetylcholine receptors in mouse primary skeletal muscle cells. Neuroscience. 128: 497-509.
Yang SY, et al. (2003) New class of ultrathin, highly cell-adhesion-resistant polyelectrolyte multilayers with micropatterning capabilities. Biomacromolecules. 4: 987-994.
Yang Y, et al. (2003) Neuronal cell death is preceded by cell cycle events at all stages of Alzheimer's disease. J Neurosci. 23: 2557-2563.
Yang Z, et al. (1999) Protein Interactions with Poly(ethylene glycol) Self-Assembled Monolayers on Glass Substrates: Diffusion and Adsorption. Langmuir. 15: 8405-8411.
Yankner BA. (1996) Mechanisms of neuronal degeneration in Alzheimer's disease. Neuron. 16: 921-932.
Yap FL and Zhang Y. (2007) Protein and cell micropatterning and its integration with micrananoparticles assembly. Biosens Bioelectron. 22: 775-788.
Yasuda SI, et al. (2001) A novel method to study contraction characteristics of a single cardiac myocyte using carbon fibers. Am J Physiol Heart Circ Physiol. 281: H1442-H1446.
Yeung CK, et al. (2007) Drug profiling using planar microelectrode arrays. Anal Bioanal Chem. 387: 2673-2680.
Yin SH, et al. (2005) Measuring single cardiac myocyte contractile force via moving a magnetic bead. Biophys J. 88: 1489-1495.
Zhao BL, et al. (1989) Scavenging effect of extracts of green tea and natural antioxidants on active oxygen radicals. Cell Biophys. 14: 175-185.

(56) References Cited

OTHER PUBLICATIONS

Zhou L, et al. (2005) Mechanistic model of cardiac energy metabolism predicts localization of glycolysis to cytosolic subdomain during ischemia. Am J Physiol Heart Circ Physiol. 288: H2400-H2411.

Zhou Z, et al. (1999) Block of HERG potassium channels by the antihistamine astemizole and its metabolites desmethylastemizole and norastemizole. J Cardiovasc Electrophysiol. 10: 836-843.

Zimmermann WH, et al. (2000) Three-dimensional engineered heart tissue from neonatal rat cardiac myocytes. Biotechnol Bioeng. 68: 106-114.

Zimmermann WH, et al. (2002) Tissue Engineering of a Differentiated Cardiac Muscle Construct. Circ Res. 90: 223-230.

Zorzano A, et al. (2003) Intracellular signals involved in the effects of insulin-A957. like growth factors and neuregulins on myofibre formation. Cell Signal. 15: 141-149.

Zurn AD, et al. (1996) Combined effects of GDNF, BDNF, and CNTF on motoneuron differentiation in vitro. J Neurosci Res. 44: 133-141.

Zweigerdt R, et al. (2003) Generation of confluent cardiomyocyte monolayers derived from embryonic stem cells in suspension: a cell source for new therapies and screening strategies. Cytotherapy. 5: 399-413.

\* cited by examiner

METHOD OF CO-CULTURING MAMMALIAN MUSCLE CELLS AND MOTONEURONS

CROSS-REFERENCE TO RELATED APPLICATION

This application is a continuation application that claims priority to U.S. nonprovisional application Ser. No. 12/765,996 filed on 23 Apr. 2010, which claims priority to U.S. provisional application Ser. No. 61/171,958 filed on 23 Apr. 2009, each of which is incorporated herein by reference in its entirety.

STATEMENT REGARDING FEDERALLY SPONSORED RESEARCH OR DEVELOPMENT

This invention was made with government support under R01 NS050452 awarded by the National Institutes of Health. The government has certain rights in the invention.

FIELD OF THE INVENTION

The present invention relates to the field of neurobiology and, more particularly, to a method of inducing formation of functional neuromuscular junctions in a co-culture of mammalian muscle cells with mammalian motoneurons which remains viable for up to approximately seven weeks.

BACKGROUND OF THE INVENTION

The neuromuscular junction (NMJ), formed between motoneurons and skeletal muscle fibers, is one of the most studied synaptic structures (Witzemann 2006). In a mammalian vertebrate, whenever an action potential is fired by a motoneuron, pre-synaptic vesicles loaded with the neurotransmitter acetylcholine (ACh) are released in the synaptic cleft (Chow et al., 1985). The released ACh diffuses across the synaptic cleft and binds to the post-synaptic terminals in the muscle enriched with receptors for acetylcholine (AChRs). This leads to muscle contraction. In this transmission process the electrical impulses (action potentials) generated by the motoneuron are converted to chemical signals, then the chemical signals are converted into a mechanical signal in the form of muscle contraction. Therefore, not only do NMJs represent an important system for studying synapse formation and maturation, but also for studying how cells interconvert messages between electrical, chemical and mechanical modalities.

In vivo, NMJ formation is a multistep process, requiring the spatial and temporal interaction of growth factors, hormones and cellular structures that results in a pre-synaptic axonal terminal interfaced with a region of the skeletal muscle membrane (postsynaptic) pre-patterned with AChRs (Colomar et al., 2004; English 2003). In vitro culture models represent a powerful cell biology tool to study the role of these different growth factors, hormones and cellular structures involved in NMJ formation in a defined, controlled system. Consequently, the development of an in vitro system resulting in NMJ formation would facilitate investigations into the roles of specific factors involved in, and required for, the process to occur efficiently.

However, limited success has been achieved in developing a long-term in vitro system for NMJ formation in the absence of serum containing media and biological substrates. These issues limit the reproducibility of in vitro studies and their translation to tissue engineering applications and high-throughput assay development. For example, the concentration and/or temporal application of medium components could be investigated to determine their influence on NMJ formation, maturation and maintenance. Such a system also benefits from the absence of factors that may be present in serum that would inhibit these processes. Employing a non-biological growth substrate such as trimethoxysilylpropyl diethylenetriamine (DETA) provides an additional measure of control. DETA is a silane molecule that forms a covalently bonded monolayer on glass coverslips, resulting in a uniform, hydrophilic surface for cell growth. The use of DETA surfaces is advantageous from a tissue engineering perspective because it can be covalently linked to virtually any hydroxolated surface, it is amenable to patterning using standard photolithography (Ravenscroft et al., 1998) and it promotes long-term cell survival because it is non-digestible by matrix metalloproteinases secreted by the cells (Das et al., 2004; Das et al., 2007 (Nat. Protocols)). It is also possible that its structural relationship to the growth factor spermidine, which has recently been shown to prolong cell life (Eisenberg et al., 2009), contribute to its unique ability to enable long-term healthy cell cultures.

Previously, we developed a defined in vitro model facilitating the short-term co-culture of motoneurons and skeletal muscle that resulted in NMJ formation (Das et al., 2007 (Neuroscience)). This model also utilized a biocompatible silane substrate and a serum-free medium formulation. However, further improvements were necessary to enhance the physiological relevance of the NMJ development system. Limitations of the previous model were that it did not support long-term tissue engineering studies and therefore, could not mimic several of the muscle maturation processes observed in vivo by obtaining myotubes that more accurately represent mature extrafusal fibers.

As noted, neuromuscular junction (NMJ) formation, occurring between motoneurons and skeletal muscle, is a complex multistep process involving a variety of signaling molecules and pathways. In vitro motoneuron-muscle co-cultures are powerful tools to study the role of different growth factors, hormones and cellular structures involved in NMJ formation. In this study we have demonstrated a co-culture system that enable sarcomere assembly in the skeletal muscle myotubes as evidenced by A band/I band formation, increased NMJ density and selective myosin heavy chain (MHC) class switching. These results suggest we have discovered a group of biomolecules that act as molecular switches promoting NMJ formation and maturation as well as skeletal muscle fiber maturation to the extrafusal phenotype. This model system will be a powerful tool in basic NMJ research, tissue engineered NMJ systems, bio-hybrid device development for limb prosthesis and in regenerative medicine. It could also be useful in new screening modalities for drug development and toxicology investigations.

SUMMARY OF THE INVENTION

With the foregoing in mind, the present invention advantageously provides a serum-free culture system utilizing defined temporal growth factor application and a non-biological substrate resulted in the formation of robust NMJs. The system resulted in long-term survival of the co-culture and selective expression of neonatal myosin heavy chain, a marker of myotube maturation. NMJ formation was verified by colocalization of dense clusters of acetylcholine receptors visualized using alpha-bungarotoxin and synaptophysin containing vesicles present in motoneuron axonal terminals.

This model will find applications in basic NMJ research and tissue engineering applications such as bio-hybrid device development for limb prosthesis and regenerative medicine as well as for high-throughput drug and toxin screening applications.

The present invention provides a method of co-culturing mammalian muscle cells and mammalian motoneurons. The method yields functional neuromuscular junctions in a culture which is particularly long-lived, up to approximately 7 weeks.

The method includes preparing one or more carriers coated with a covalently bonded monolayer of trimethoxysilylpropyl diethylenetriamine (DETA). The carriers are preferably glass cover slips as used for microscopy applications. The method continues by suspending isolated fetal mammalian skeletal muscle cells in serum-free medium according to medium composition 1, followed by suspending isolated fetal mammalian spinal motoneurons in serum-free medium according to medium composition 1. Next is plating the suspended muscle cells onto the one or more carriers at a predetermined density and allowing the muscle cells to attach and plating the suspended motoneurons at a predetermined density onto the one or more carriers and allowing the motoneurons to attach. The method continues by then covering the one or more carriers with a mixture of medium composition 1 and medium composition 2 and incubating the carriers covered in the media mixture.

It is preferable that in carrying out the presently disclosed method, the practitioner verify DETA monolayer formation by one or more optical parameters, for example, with a contact angle goniometer and by X-ray photoelectron spectroscopy (XPS).

In the method, the mammalian skeletal muscle cells and mammalian spinal motoneurons preferably originate from fetal rats. In this regard, when plating the muscle cells it is preferably done at a density of approximately from 700 to 1000 cells/mm$^2$ and the motoneurons are preferably plated at a density of approximately 100 cells/mm$^2$. It should be understood that incubating is effected under mammalian physiologic conditions, as is known in the art for mammalian cell tissue culture. Particularly, incubating is best effected at approximately 37° C. in an air atmosphere with about 5% $CO_2$ and 85% humidity.

In the method, covering comprises a mixture of approximately equal volumes of medium composition 1 and medium composition 2. A complete change of the medium covering the carriers by substituting NbActiv4 medium without growth factors is preferred during the first week of incubation and most preferred on day 4 of incubation. Afterwards, the method calls for changing spent medium as needed with fresh NbActiv4 medium without growth factors. In a preferred embodiment of the method, this periodic changing of the medium may be accomplished every 3 days.

In another embodiment of the presently disclosed method, co-culturing mammalian muscle cells and motoneurons includes allowing fetal muscle cells and fetal spinal motoneurons suspended in a serum-free medium according to composition 1 to adhere to a monolayer of covalently bonded DETA supported on an underlying carrier surface. Following this, the method calls for incubating the adhered muscle cells and motoneurons covered in a mixture of serum-free medium composition 1 and serum-free medium composition 2. Further details of this alternate embodiment are as noted above.

Yet another embodiment or variation of the present invention includes a method of inducing in vitro formation of functional neuromuscular junctions. This embodiment includes depositing a suspension of isolated fetal muscle cells and fetal spinal motoneurons in a mixture of medium compositions 1 and 2 onto a film of DETA supported on a carrier surface, allowing the cells to adhere to the film and culturing the cells under mammalian physiologic conditions. This is followed by changing the medium mixture to medium composition 2 without growth factors before seven days of culturing the cells, and exchanging spent medium during culturing for fresh medium composition 2 without growth factors. The method also includes monitoring the cells while culturing for formation of functional neuromuscular junctions between motoneurons and muscle cells.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF PREFERRED EMBODIMENTS

Figure 1:
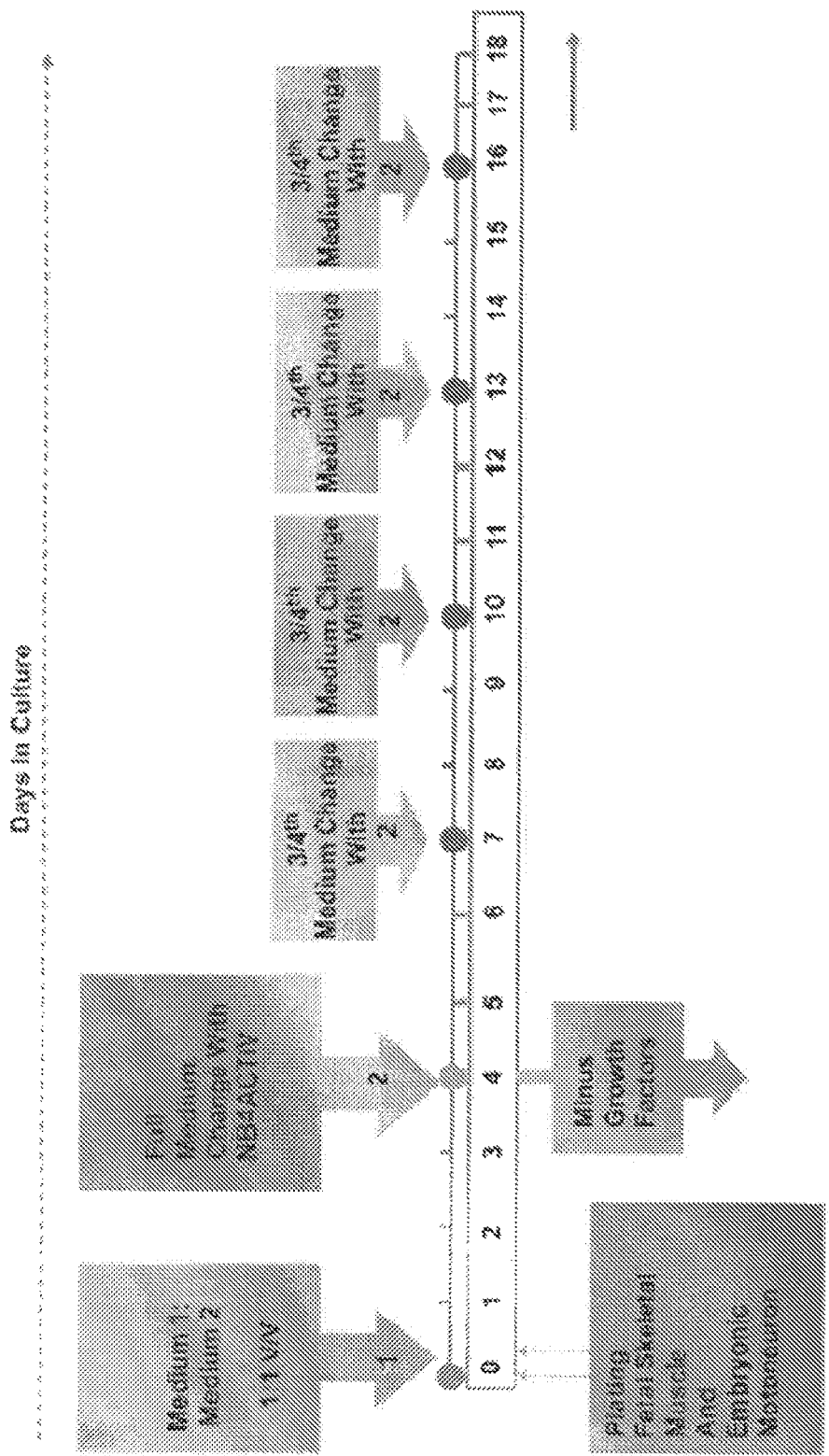
FIG. 1 is a protocol for long-term NMJ formation in a motoneuron and skeletal muscle co-culture, according to an embodiment of the present invention.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Materials and Methods
Surface Modification and Characterization

Glass coverslips (Thomas Scientific 6661F52, 22×22 mm No. 1) were cleaned using an O2 plasma cleaner (Harrick PDC-32G) for 20 min at 100 mTorr. The DETA (United Chemical Technologies Inc. T2910KG) films were formed by the reaction of the cleaned glass surface with a 0.1% (v/v) mixture of the organosilane in freshly distilled toluene (Fisher T2904). The DETA coated coverslips were then heated to approximately 100° C., rinsed with toluene, reheated to approximately 100° C., and then oven dried (Das et al., 2006). Surfaces were characterized by contact angle measurements using an optical contact angle goniometer (KSV Instruments, Cam 200) and by X-ray photoelectron spectroscopy (XPS) (Kratos Axis 165). XPS survey scans, as well as high-resolution N1s and C1s scans utilizing monochromatic AI Ka excitation were obtained (Das et al., 2006).

Skeletal Muscle Culture in Serum-Free Medium

Skeletal muscle was dissected from the thighs of the hind limbs of fetal rat (17e18 days old). Briefly, rats were anaesthetized and killed by inhalation of an excess of $CO_2$. This procedure was in agreement with the Animal Research Council of University of Central Florida, which adheres to IACUC policies. The tissue was collected in a sterile 15 mL centrifuge tube containing 1 mL phosphate-buffered saline (calcium- and magnesium-free) (Gibco 14200075). The tissue was enzymatically dissociated using 2 mL of 0.05% of trypsin-EDTA (Gibco 25300054) solution for 30 min in a 37° C. water bath at 50 rpm. After 30 min the trypsin solution was removed and 4 mL Hibernate E/10% fetal bovine serum (Gibco 16000044) was added to terminate the trypsin reaction. The tissue was then mechanically triturated with the supernatant being transferred to a 15 mL centrifuge tube. The same process was repeated two times by adding 2 mL of L15/10% FBS each time. The 6 mL cell suspension obtained after mechanical trituration was suspended on a 2 mL, 4% BSA (Sigma A3059) (prepared in L15 medium) cushion and centrifuged at 300 g for 10 min at 4° C. The pellet obtained was washed 5 times with L15 medium then resuspended in 10 mL of L15 and plated in 100 mm uncoated dishes for 30 min. The non-attached cells were removed and then centrifuged on a 4% BSA cushion (Das et al., 2006).

The pellet was resuspended in serum-free medium according to the protocol illustrated in FIG. 1 and plated on the coverslips at a density of 700-1000 cells/mm$^2$. The serum-free medium containing different growth factors and hormones was added to the culture dish after 1 h. The final medium was prepared by mixing medium 1 (Table 1) and medium 2 (Table 2) in a 1:1 v/v ratio. FIG. 1 indicates a flowchart of the culture protocol. Tables 1 and 2 list the growth factor and hormone supplement compositions of medium one and medium two. The cells were maintained in a 5% CO2 incubator (relative humidity 85%). The entire medium was replaced after four days with NbActiv4 medium according to the protocol in FIG. 1 (Brewer et al., 2008). As described in (Brewer et al., 2008), NbActiv4™ (available from BrainBits LLC) comprises all of the ingredients in Neurobasal™ (Table 3), B27™ (Table 4), and Glutamax™ (Table 5). NbActiv4™ may also comprise creatine, estrogen, and cholesterol. Thereafter three-fourths of the medium was changed every three days with NbActiv4™.

TABLE 1

Composition of Medium 1

| No. | Component | Amount | Catalogue # | Source | References |
|---|---|---|---|---|---|
| 1 | Neurobasal A | 500 mL | 10888 | Gibco/Invitrogen | Brewer et al., 1993 |
| 2 | Antibiotic-Antimycotic | 5 mL | 15240-062 | Gibco/Invitrogen | |
| 3 | Glutamax | 5 mL | 35050-061 | Gibco/Invitrogen | |
| 4 | B27 Supplement | 10 mL | 17504-044 | Gibco/Invitrogen | Das et al., 2004; Brewer et al., 1993 |
| 5 | G5 Supplement (100X) | 5 mL | 17503-012 | Gibco/Invitrogen | Alterio et al., 1990; Clegg et al., 1987; Bottenstein 1981, 1988; Bottenstein et al., 1988; Morrow et al., 1990; Gonzalez et al., 1990; |

TABLE 1-continued

Composition of Medium 1

| No. | Component | Amount | Catalogue # | Source | References |
|---|---|---|---|---|---|
| 6 | VEGF$_{165\ r\ Human}$ | 10 μg | P2654 | Gibco/Invitrogen | Moore et al., 1991; Anderson et al., 1991; Olwin et al., 1992 Arsic et al., 2004; Germani et al., 2003; Lee et al., 2003; Lescaudron et al., 1999 |
| 7 | Acidic FGF | 12.5 μg | 13241-013 | Gibco/Invitrogen | Alterio et al., 1990; Moore et al., 1991; Olwin et al., 1992; Motamed et al., 2003; Dusterhoft et al., 1999; Fu et al., 1995; Smith et al., 1994; Oliver et al., 1992; Dell'Era et al., 2003 |
| 8 | Heparin Sulphate | 50 μg | D9809 | Sigma | Alterio et al., 1990; Moore et al., 1991; Olwin et al., 1992; Motamed et al., 2003; Dusterhoft et al., 1999; Fu et al., 1995; Smith et al., 1994; Oliver et al., 1992; Dell'Era et al., 2003 |
| 9 | LIF | 10 μg | L5158 | Sigma | Husmann et al., 1996; Kurek et al., 1996; Megeney et al., 1996; Vakakis et al., 1995; Martinou et al., 1992; Sun et al., 2007; Malm et al., 2004; Zorzano et al., 2003; Sakuma et al., 2000 |
| 10 | Vitronectin (Rat Plasma) | 50 μg | V0132 | Sigma | Biesecker 1990; Gullberg et al., 1995 |
| 11 | CNTF | 20 μg | CRC 401B | Cell Sciences | Wang et al., 2008; Chen et al., 2003, 2005; Cannon 1998; Marques et al., 1997 |
| 12 | NT 3 | 10 μg | CRN 500B | Cell Sciences | Oakley et al., 1997 |
| 13 | NT 4 | 10 μg | CRN 501B | Cell Sciences | Carrasco et al., 2003; Simon et al., 2003 |
| 14 | GDNF | 10 μg | CRG 400B | Cell Sciences | Choi-Lundberg et al., 1995; Lin et al., 1993; Yang et al., 2004; Golden et al., 1999; Henderson et al., 1994 |
| 15 | BDNF | 10 μg | CRB 600B | Cell Sciences | Simon et al., 2003; Heinrich 2003; Mousavi et al., 2004 |
| 16 | CT-1 | 10 μg | CRC 700B | Cell Sciences | Chen et al., 2004; Bordet et al., 2001; Dolcet et al., 2001; Lesbordes et al., 2002; Nishikawa et al., 2005; Mitsumoto et al., 2001; Oppenheim et al., 2001; Peroulakis et al., 2000; Sheng et al., 1996 |

TABLE 2

Composition of Medium 2

| No. | Component(s) | Amount | Catalogue | Source | References |
|---|---|---|---|---|---|
| 1 | Neurobasal A | 500 mL | 10888 | Invitrogen/Gibco | Brewer et al., 1993 |
| 2 | Glutamax | 5 mL | 35050-061 | Invitrogen/Gibco | |
| 3 | Antibiotic-Antimycotic | 5 mL | 15240-062 | Invitrogen/Gibco | |

TABLE 2-continued

Composition of Medium 2

| No. | Component(s) | Amount | Catalogue | Source | References |
|---|---|---|---|---|---|
| 4 | B27 Supplement | 10 mL | 17504-044 | Invitrogen/Gibco | Das et al., 2004; Brewer et al., 1993 |
| 5 | Cholesterol (250X) | 5 mL | 12531 | Invitrogen/Gibco | Jaworska-Wilczynska et al., 2002 |
| 6 | TNF-alpha, human | 10 μg | T6674 | Sigma-Aldrich | Caratsch et al., 1994; Al-Shanti et al., 2008; Miller et al., 1988 |
| 7 | PDGF BB | 50 μg | P4056 | Sigma-Aldrich | Husmann et al., 1996; Jin et al., 1991; Kudla et al., 1995; Quinn et al., 1990; Yablonka-Reuveni et al., 1995 |
| 8 | Vasoactive intestinal peptide (VIP) | 250 μg | V6130 | Sigma-Aldrich | Gold 1982 |
| 9 | Insulin-like growth factor 1 | 25 μg | 12656 | Sigma-Aldrich | Malm et al., 2004; Zorzano et al., 2003; Al-Shanti et al., 2008 |
| 10 | NAP | 1 mg | 61170 | AnaSpec. Inc. | Gozes et al., 2004; Aracil et al., 2004 |
| 11 | Recombinant Apolipoprotein E2 | 50 μg | P2002 | Panvera | Robertson et al., 2000 |
| 12 | Laminin, mouse purified | 2 mg | 08-125 | Millipore | Langen et al., 2003; Foster et al., 1987; Hantai et al., 1991; Kuhl et al., 1986; Lyles et al., 1992; Song et al., 1992; Swasdison et al., 1992 |
| 13 | Beta amyloid (1-40) | 1 mg | AG966 | Millipore | Wang et al., 2005; Yang et al., 2007; Akaaboune et al., 2000 |
| 14 | Human Tenascin-C protein | 100 μg | CC065 | Millipore | Hall et al., 2000 |
| 15 | rr-Sonic hedgehog, Shh N-terminal | 50 μg | 1314-SH | R&D Systems | Fan et al., 1994; Munsterberg et al., 1995; Nelson et al., 1996; Cossu et al., 1996; Currie et al., 1996; Norris et al., 2000; Brand-Saberi et al., 2005; Elia et al., 2007; Pagan et al., 1996; Bren-Mattison et al., 2002; Maves et al., 2007; Koleva et al., 2005 |
| 16 | rr (Agrin C terminal) | 50 μg | 550-AG-100 | R&D Systems | Bandi et al., 2008; Sanes 1997 |

TABLE 3

Composition of Neurobasal™ medium

| No. | Components | Molecular Weight | Concentration (mg/L) | Concentration (mM) |
|---|---|---|---|---|
| 1 | Glycine | 75 | 30 | 4.00E−01 |
| 2 | L-Alanine | 89 | 2 | 2.25E−02 |
| 3 | L-Arginine hydrochloride | 211 | 84 | 3.98E−01 |
| 4 | L-Asparagine-$H_2O$ | 150 | 0.83 | 5.53E−03 |
| 5 | L-Cysteine | 121 | 31.5 | 2.60E−01 |
| 6 | L-Histidine hydrochloride-$H_2O$ | 210 | 42 | 2.00E−01 |
| 7 | L-Isoleucine | 131 | 105 | 8.02E−01 |
| 8 | L-Leucine | 131 | 105 | 8.02E−01 |
| 9 | L-Lysine hydrochloride | 183 | 146 | 7.98E−01 |
| 10 | L-Methionine | 149 | 30 | 2.01E−01 |
| 11 | L-Phenylalanine | 165 | 66 | 4.00E−01 |
| 12 | L-Proline | 115 | 7.76 | 6.75E−02 |
| 13 | L-Serine | 105 | 42 | 4.00E−01 |
| 14 | L-Threonine | 119 | 95 | 7.98E−01 |
| 15 | L-Tryptophan | 204 | 16 | 7.84E−02 |
| 16 | L-Tyrosine | 181 | 72 | 3.98E−01 |
| 17 | L-Valine | 117 | 94 | 8.03E−01 |
| 18 | Choline chloride | 140 | 4 | 2.86E−02 |
| 19 | D-Calcium pantothenate | 477 | 4 | 8.39E−03 |
| 20 | Folic Acid | 441 | 4 | 9.07E−03 |
| 21 | Niacinamide | 122 | 4 | 3.28E−02 |
| 22 | Pyridoxal hydrochloride | 204 | 4 | 1.96E−02 |
| 23 | Riboflavin | 376 | 0.4 | 1.06E−03 |
| 24 | Thiamine hydrochloride | 337 | 4 | 1.19E−02 |
| 25 | Vitamin B12 | 1355 | 0.0068 | 5.02E+06 |
| 26 | i-Inositol | 180 | 7.2 | 4.00E−02 |
| 27 | Calcium Chloride (CaCl2) (anhyd.) | 111 | 200 | 1.80E+00 |

TABLE 3-continued

Composition of Neurobasal ™ medium

| No. | Components | Molecular Weight | Concentration (mg/L) | Concentration (mM) |
|---|---|---|---|---|
| 28 | Ferric Nitrate (Fe(NO3)3"9H2O) | 404 | 0.1 | 2.48E+04 |
| 29 | Magnesium Chloride (anhydrous) | 95 | 77.3 | 8.14E−01 |
| 30 | Potassium Chloride (KCl) | 75 | 400 | 5.33E+00 |
| 31 | Sodium Bicarbonate (NaHCO3) | 84 | 2200 | 2.62E+01 |
| 32 | Sodium Chloride (NaCl) | 58 | 3000 | 5.17E+01 |
| 33 | Sodium Phosphate monobasic (NaH2PO4H2O) | 138 | 125 | 9.06E−01 |
| 34 | Zinc sulfate (ZnSO47H2O) | 288 | 0.194 | 6.74E+04 |
| 35 | D-Glucose (Dextrose) | 180 | 4500 | 2.50E+01 |
| 36 | HEPES | 238 | 2600 | 1.09E+01 |
| 37 | Phenol Red | 376.4 | 8.1 | 2.15E−02 |
| 38 | Sodium Pyruvate | 110 | 25 | 2.27E−01 |

TABLE 4

Composition of B27 ™

| No. | Component | Concentration (mg/L) |
|---|---|---|
| 1 | L-Alanine | 2.00E+00 |
| 2 | L-Glutamate | 3.70E+00 |
| 3 | L-Glutamine | 4.41E+02 |
| 4 | L-Proline | 7.76E+00 |
| 5 | Biotin | 1.00E−01 |
| 6 | Vitamin B12 | 3.40E−01 |
| 7 | Corticosterone | 2.00E−02 |
| 8 | Progesterone | 6.30E−03 |
| 9 | Retinol, all trans (Vit. A) | 1.00E−01 |
| 10 | Retinol, acetate | 1.00E−01 |
| 11 | Insulin | 4.00E+00 |
| 12 | T3 (triodo-L-thyronine) | 2.00E−03 |
| 13 | Na pyruvate | 2.50E+01 |
| 14 | Lipoic acid (thioctic acid) | 4.70E−02 |
| 15 | D,L-α-Tocopherol (vit. E) | 1.00E+00 |
| 16 | D,L-α-Tocopherol acetate | 1.00E+00 |
| 17 | Catalase | 2.50E+00 |
| 18 | Glutathione (reduced) | 1.00E+00 |
| 19 | Superoxide dismutase | 2.50E+00 |
| 20 | L-Carnitine | 2.00E+00 |
| 21 | Ethanolamine | 1.00E+00 |
| 22 | D(+)-Galactose | 1.50E+01 |
| 23 | HEPES | 2.60E+03 |
| 24 | Putrescine | 1.61E+01 |
| 25 | Penicillin | 50 IU/mL |
| 26 | Streptomycin | 5.00E−01 |
| 27 | Selenium | 1.60E−02 |
| 28 | Zinc sulfate | 1.94E−01 |
| 29 | Linoleic acid | 1.00E+00 |
| 30 | Linolenic acid | 1.00E+00 |
| 31 | Albumin, bovine | 2.50E+03 |
| 32 | Transferrin | 5.00E+00 |

TABLE 5

Composition of GlutaMax ™

| No. | Component | Concentration |
|---|---|---|
| 1 | L-alanyl-L-glutamine dipeptide | 200 mM |
| 2 | NaCl | 0.85% |

Rat Embryonic Motoneuron Isolation and Co-Culture

Rat spinal motoneurons were purified from ventral cords of embryonic day 14 (E14) embryos. Briefly, rats were anaesthetized and killed by inhalation of an excess of $CO_2$. This procedure was in agreement with the Animal Research Council of University of Central Florida, which adheres to IACUC policies. Ventral spinal cord cells from the embryo were collected in cold Hibernate E/GlutaMAX/antibiotic-antimycotic/B27. The cells were dissociated with 0.05% trypsin-EDTA (Invitrogen) treatment for 15 min. The dissociated cells were layered over a 4 mL step gradient Optiprep diluted 0.505:0.495 (v/v) with Hibernate E/GlutaMAX/antibiotic-antimycotic/B27 and then made to 15%, 20%, 25% and 35% (v/v) in Hibernate E/GlutaMAX/antibiotic-anti-mycotic/B27 followed by centrifugation for 15 min, using 200 g at 4° C. After centrifugation, four bands of cells were obtained. The motoneurons with large somas constituted the uppermost band. These cells present in the uppermost band were collected in fresh Hibernate E/GlutaMAX/antibiotic-anti-mycotic/B27 and centrifuged for 5 min at 200 g and 4° C. The pelleted motoneurons were re-suspended in plating medium then plated on top of muscle cells at a density of 100 cells/mm$^2$. Motoneuron plating was performed 30 min after plating of the muscle cells.

Immunocytochemistry

Neonatal Myosin Heavy Chain (Neonatal MHC)

Coverslips were rinsed with PBS, fixed in 20° C. methanol for 5-7 min, washed in PBS, incubated in PBS supplemented with 1% BSA and 0.05% saponin (permeabilization solution), and blocked for 30 min in a permeabilization solution+10% goat serum (blocking solution). Cells were incubated overnight with primary antibody against neonatal MHC (N3.36, IgG, Developmental Studies Hybridoma Bank) diluted (1:5) in the blocking solution. Cells were washed with PBS and incubated with AlexaFluor secondary antibody (Invitrogen) (diluted in PBS) for 2 h. The secondary antibody solution was removed and the cells were rinsed using PBS. The coverslips were dried and mounted on glass slides using VectaShield+DAPI mounting medium (Vector Laboratories H-1200) and viewed on a confocal microscope (UltraVIEW LCI, PerkinElmer).

Double Staining with Neurofilament 150 and Neonatal Myosin Heavy Chain

Co-cultures were processed for immunocytochemistry as described above. Next, cells were incubated overnight at 4° C. with rabbit anti-neurofilament M polyclonal antibody, 150 kD, (Chemicon, AB1981, diluted 1:2000) and neonatal MHC (N3.36, IgG, Developmental Studies Hybridoma Bank diluted 1:5). After overnight incubation, the coverslips were rinsed three times with PBS and then incubated with the AlexaFluor secondary antibodies (Invitrogen) for 2 h. After rinsing three times in PBS, the coverslips were mounted with Vectashield+DAPI mounting medium onto glass slides. The coverslips were visualized and images collected using a confocal microscope (UltraVIEW LCI, PerkinElmer). Controls without primary antibody were negative.

AChR+Synaptophysin Co-Staining

AChRs were labeled as described previously by incubating cultures with $5 \times 10^{-8}$ M of α-bungarotoxin, Alexa Fluor® 488 conjugate (Molecular Probes, B-13422) for 1.5 h at 37° C. before observation (Das et al., 2007 (Neuroscience)). Labeled cultures were fixed with glacial acetic acid and ethanol, washed with PBS, dried, mounted and examined by confocal microscopy. The coverslips which were used for double staining with AChR+synaptophysin for locating the NMJs were processed further. After 1.5 h of α-bungarotoxin labeling of the AChR receptors, the coverslips were fixed, blocked, permeabilized and incubated overnight with synaptophysin antibody (MAB368, diluted 1:1000; Millipore/Chemicon), the pre-synaptic marker present in motoneuron axonal terminals.

Data Analysis

Statistics were calculated using the following procedure. One coverslip was randomly selected from each experiment (typically, there are six coverslips per experiment). 25 non-overlapping fields of view were used to characterize each coverslip. At the magnification used, 25 fields covers over 40% of the surface area of the coverslip.

Results

DETA Surface Modification and Characterization

Static contact angle and XPS analysis were used for the validation of the surface modifications and for monitoring the quality of the surfaces. Stable contact angles (40.64°±2.9/mean±SD) throughout the study indicated high reproducibility and quality of the DETA surfaces and these characteristics were similar to previously published results (Das et al., 2004; Das et al., 2007 (Nat. Protocols); Das et al., 2007 (Neuroscience); Das et al., 2006; Das et al., 2003). Based on the ratio of the N is (401 and 399 eV) and the Si $2p_{3/2}$ peaks, XPS measurements indicated that a reaction-site limited monolayer of DETA was formed on the coverslips (Stenger et al., 1992).

Temporal Growth Factor Application

The formation of the maximal number of neuromuscular junctions was observed using the temporal growth factor application technique described in FIG. 1. Upon plating of the motoneurons and skeletal muscle, the cells were treated with medium containing factors that promoted both growth and survival as well as enhancement of NMJ formation (Table 1, Table 2). After 3 days in culture, the entire medium was removed and switched to a minimal formulation, NbActiv4, which facilitated both long-term survival and further development of the NMJs (FIG. 1). Further, three-fourths of the NbActiv4 medium per well was removed and replaced with an equal volume of fresh NbActiv4 medium. When compared to the continuous application of growth factors, the timed application resulted in cultures that lasted for up to 7 weeks as opposed to 10-12 days.

Culture Morphology of Motoneuron and Skeletal Muscle Myotube Interactions

Figure 2:
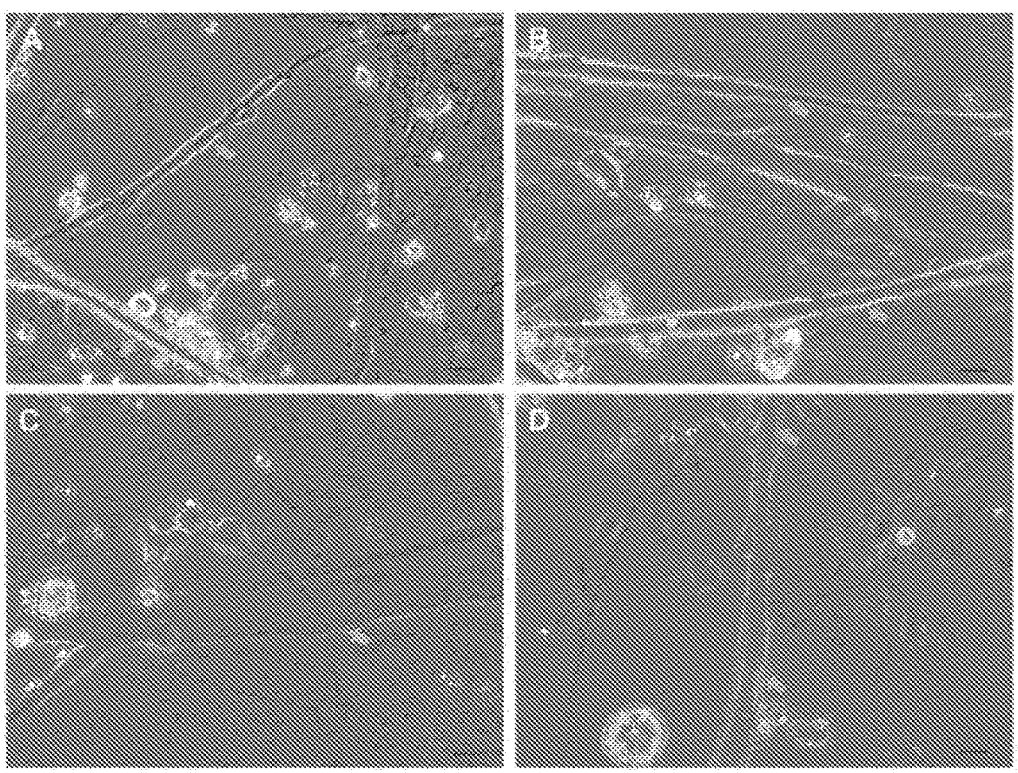
FIG. 2 shows phase contrast micrographs of the motoneuron and skeletal muscle co-culture between days 12-15. (A-D); red arrows indicate the distinct morphology of the motoneuron and its processes; green arrows indicate the myotubes; scale bar=25 µm.
Figure 3:
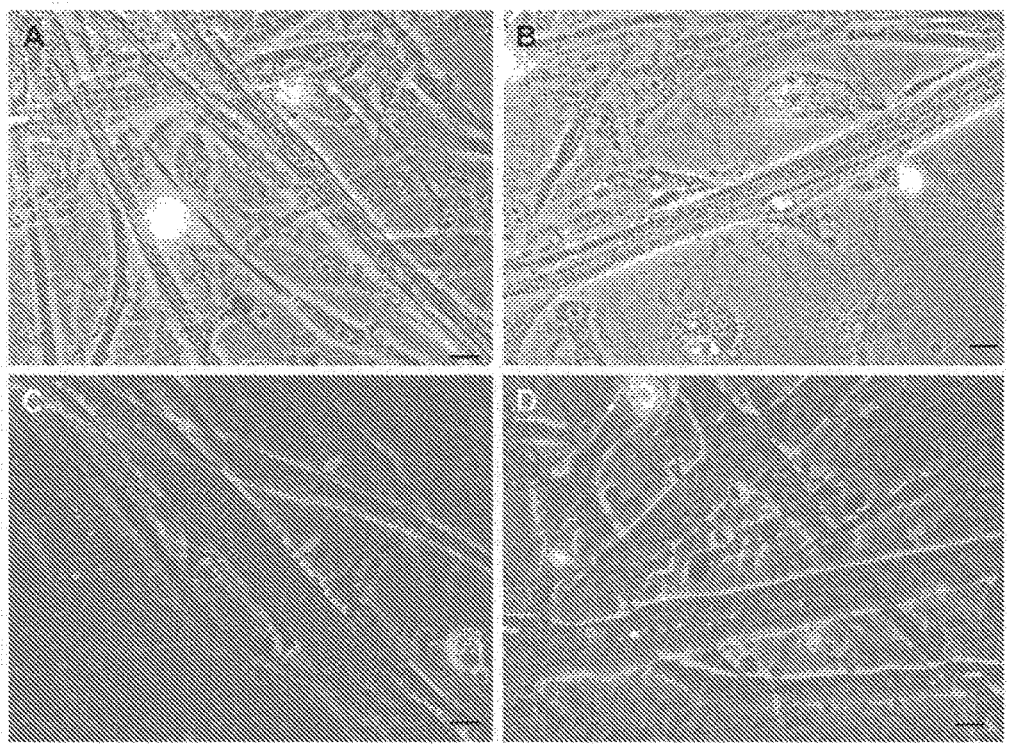
FIG. 3 provides phase contrast pictures of the co-cultures between days 25-30; (A, B) the myotubes exhibited characteristic striations; (C, D) myotubes with striations and myotubes without striations; red arrows indicate the motoneuron cell body and the processes; green arrows indicate the myotubes; scale bar for A, B=40 µm; scale bar for C, D=25 µm.

Phase contrast microscopy was used to visualize motoneuron axons appearing to interact with skeletal muscle myotubes between days 12-15 (FIG. 2, A-D). Some of the axonal processes appear to branch and terminate on the myotubes. Furthermore, many of the myotubes exhibited characteristic striation patterns observed after sarcomere formation when the fibers reached approximately 25-30 days in culture (FIG. 3, A-D). Quantification of the appearance of striations after this time indicated that the co-cultures contained about twice the number of myotubes showing striations.

Figure 4:
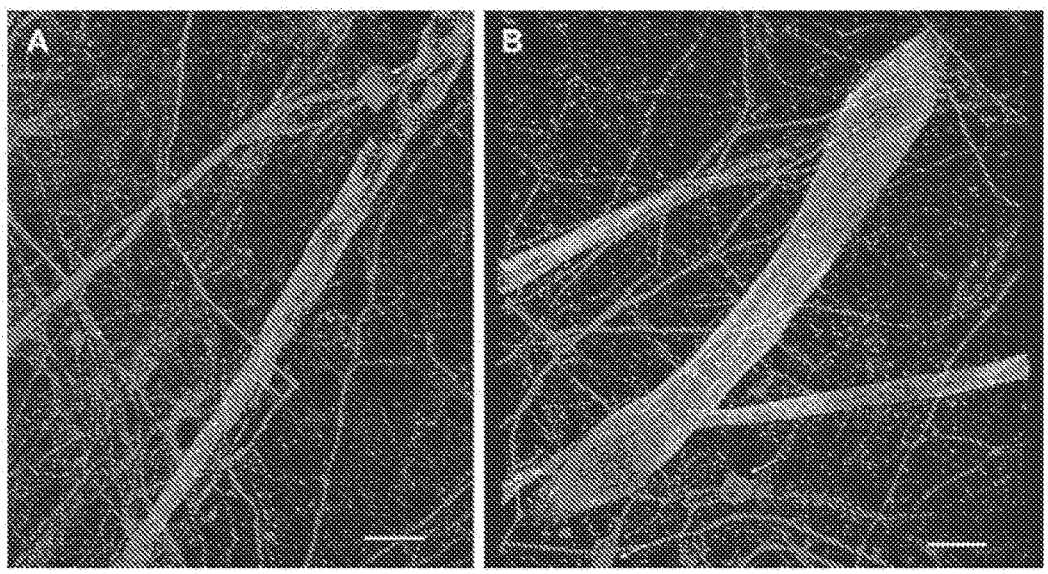
FIG. 4 shows the immunocytochemistry of co-cultures at day 25; (A-B) NF-150 (red) indicates the large motoneurons and their processes (white arrows); the striated myotubes (green) stained for nMHC (N3.36); scale bar=50 µm.

Immunocytochemical Characterization of Motoneuron and Skeletal Muscle Co-Culture The characteristic protein expression patterns of the motoneurons and myotubes in co-culture were evaluated at day 25. Immunocytochemistry was used to visualize the neurofilament protein expression in the motoneurons and neonatal myosin heavy chain (MHC) expression for the myotubes (FIG. 4, A-B). Motoneuron processes were clearly indicated interacting with the skeletal muscle myotubes. A band/I band formation was more visible in the myotubes after staining with the neonatal myosin heavy chain antibody. The immunocytochemical analysis supported the morphological analysis, which had indicated the presence of striations in double the number of myotubes as observed with the muscle only controls.

Neuromuscular Junction Formation

Figure 5:
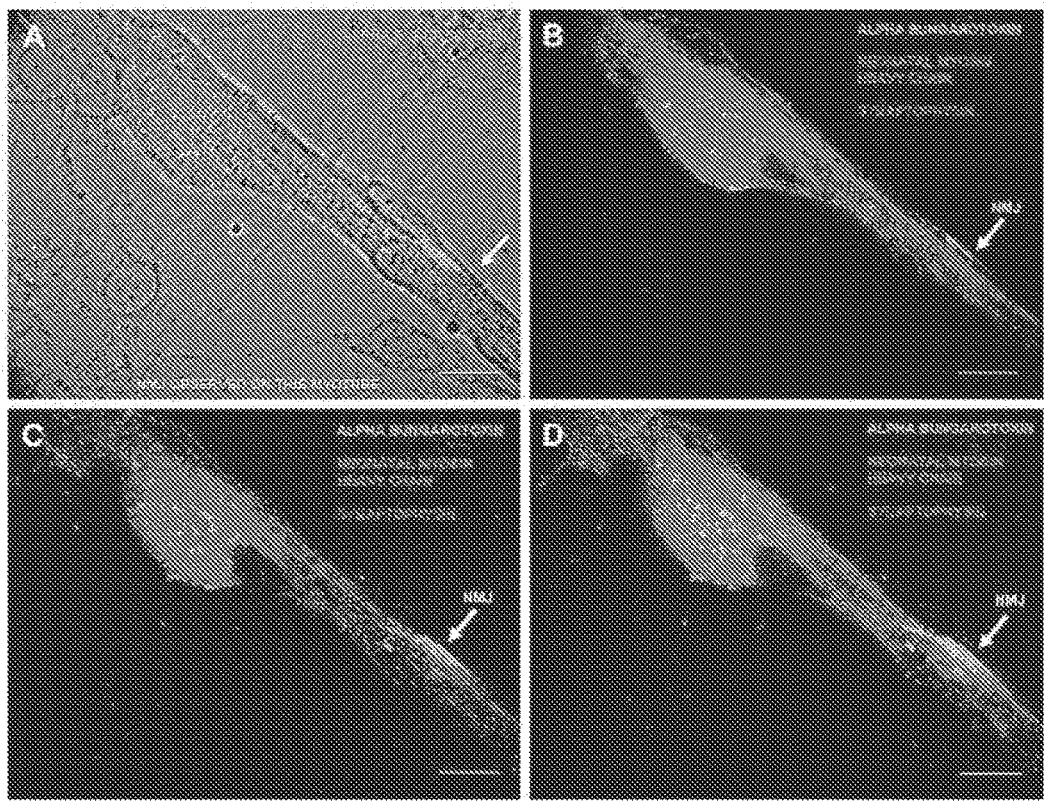
FIG. 5 depicts neuromuscular junction (NMJ) formation between day 30-40; (A) phase picture of the myotube indicating the alpha-bungarotoxin staining in green; (B) triple stain, showing the close proximity of alpha-bungarotoxin (green) and synaptophysin (blue) indicating synapse formation at a specific confocal plane and myotube striations are indicated in red (nMHC); (C-D) NMJ observed at two different planes using confocal microscopy; a much more dense clustering of synaptophysin and alpha-bungarotoxin was observed in these planes.
Figure 6:
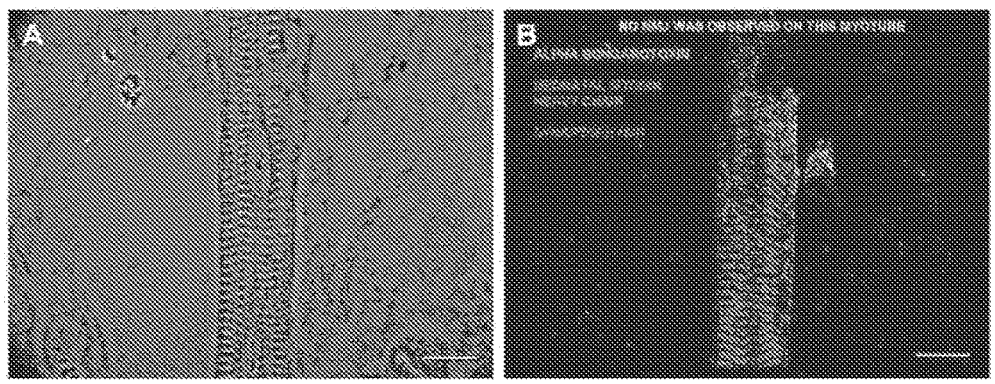
FIG. 6 shows striated myotube development in the absence of NMJ formation; (A, B) no NMJs were observed on this striated myotube; (A) a phase picture of the myotube; (B) immunostained picture of the same myotube with alpha-bungarotoxin, N3.36 and synaptophysin; scale bar=50 µm.
Figure 7:
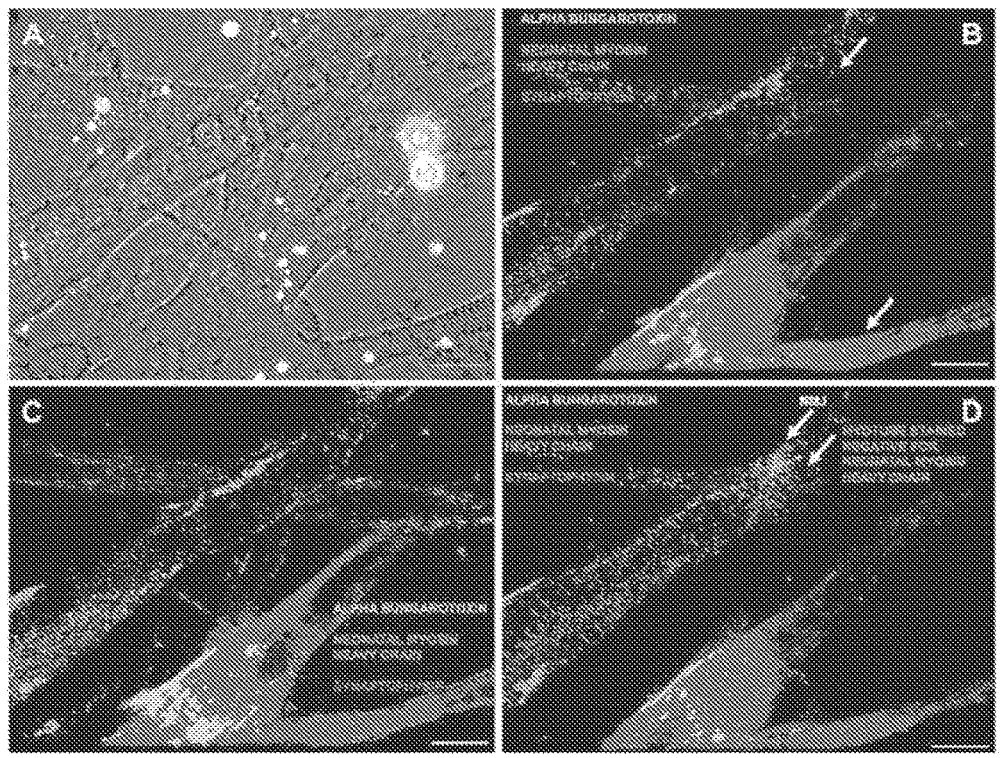
FIG. 7 depicts NMJ formation on an N3.36 (−) myotube; (A) phase picture showing the different morphologies of myotubes in the co-culture; (B-D) show that NMJ formation was observed on a myotube that was negative for N3.36; culture stained with alpha-bungarotoxin, N3.36 and synaptophysin; possibly the myotube on which NMJ was formed was immature and had not yet expressed the neonatal myosin heavy chain marker (N3.36).

In order to determine neuromuscular junction formation using this novel medium formulation, the clustering of AChRs using alpha-bungarotoxin and their colocalization with synaptophysin vesicles was analyzed immunocytochemically. The colocalization of these two synaptic markers indicated the proximity of pre-synaptic and post-synaptic structures and was a positive indication of NMJ formation. This technique was used to identify the colocalization of synaptophysin vesicles with the AChR clusters (FIG. 5, A-D). The axon+myotube interactions that did not result in the colocalization of pre-synaptic and post-synaptic structures were also identified (FIG. 6, A-B). The observation of the negative result defines the difference between colocalization and non-colocalization and emphasizes the positive result observed in this system. FIG. 7 illustrates NMJ formation between a myotube in culture that did not stain for neonatal myosin heavy chain and a motoneuron.

Discussion

This work documents the substantial improvement of an in vitro model system for NMJ formation. Specifically, we observed enhanced survivability of the culture resulting in our ability to conduct long-term studies on the motoneuron-skeletal muscle cocultures. This increased survivability resulted in maturation of the skeletal muscle myotubes and a significant improvement in the number of NMJs formed in culture.

Previously, we developed the first defined culture model to coculture embryonic motoneuron and fetal skeletal muscle, however this model was not suitable for long-term tissue engineering studies and the myotubes in the culture only expressed an early muscle marker, i.e. fetal myosin heavy chain and none of the myotubes exhibited characteristic striations. In this study, significant improvement over our previous motoneuron-skeletal muscle co-culture model system was documented. This new culture model supported long-term co-culture of both motoneuron and muscle, resulted in a more adult-like morphology of the muscle and a higher density of neuromuscular junctions (NMJ). Our findings were supported by morphological and immunocytochemical data.

We developed this serum-free medium, supplemented with growth factors that supported the survival, proliferation and fusion of fetal rat myoblasts into contractile myotubes, in a semi-empirical fashion. The rationale for selecting the growth factors was based on the distribution of their cognate receptors in the developing myotubes in rat fetus (Arnold et al., 1998; Brand-Saberi et al., 2005; Olson et al., 1992). Tables 1 and 2 reference the literature where these individual growth factors, hormones and neurotransmitters were observed to support muscle and neuromuscular junction development. The composition in Table 1 is the formulation used for a previously published medium utilized for motoneuron-muscle co-culture and adult spinal cord neuron culture (Das et al., 2007 (Neuroscience); Das et al., 2008 (Exp. Neurology); Das et al., 2005; Das et al., 2007 (Biomaterials)). Table 2 lists the twelve additional factors identified in muscle development and neuromuscular junction formation that enabled the increased survivability of the system. Further addition of the factors in Table 2 promoted formation of characteristic striation in the muscle in the culture. The use of NbActiv4 for the maintenance of the cells significantly improved the survival of the skeletal muscle derived myotubes despite the fact that the original purpose of the development of NbActiv4 was for the long-term maintenance and synaptic connectivity of fetal hippocampal neurons in vitro (Brewer et al., 2008).

In our previous co-culture model, we did not observe the expression of neonatal MHC proteins in the myotubes. Interestingly, when this same medium and protocol was used to culture pure skeletal muscle we observed certain striking differences. The pure muscle culture survived longer, exhibited characteristic striations, but only a very small percentage of myotubes expressed N3.36 (Das et al., 2009 (Biomaterials)). To the best of our understanding, the N3.36 expression in skeletal muscle in culture is influenced by the motoneurons either physically or by certain trophic factors secreted in the presence of this modified medium and NbActiv4. This observation needs further studies in order to dissect the molecular pathways regulating N3.36 expression in pure skeletal muscle culture and in skeletal muscle-motoneuron co-culture. Also, the potential regulation of MHC class switching independent of neuronal innervation/denervation represents an interesting topic for further study. This system would have applications in developing therapies for muscle-nerve diseases such as ALS, spinal muscular atrophy, spinal cord injury and myasthenia gravis.

Conclusions

The development of robust NMJ formation, long-term survival of motoneuron þ skeletal muscle co-cultures and selective MHC class switching is documented in this research. This improved system supports the goal of creating a physiologically relevant tissue engineered motoneuron þ skeletal muscle construct and puts within reach the goal of developing functional bio-hybrid devices to analyze NMJ activity. This defined model can also be used to map the developmental pathways regulating NMJ formation and MHC class switching. Furthermore, we believe this serum free culture system will be a powerful tool in developing advanced strategies for regenerative medicine in ALS, stretch reflex arc development and integrating motoneuron+ skeletal muscle with bio-hybrid prosthetic devices. Due to the use of a serum-free defined culture system this also has applications for new high-throughput screening systems for use in drug discovery research and toxicology investigations.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES CITED

[1] Akaaboune M, et al. (2000) Developmental regulation of amyloid precursor protein at the neuromuscular junction in mouse skeletal muscle. Mol Cell Neurosci. 15(4):355-367.
[2] Al-Shanti N, et al. (2008) Beneficial synergistic interactions of TNF.alpha and IL.6 in C2 skeletal myoblasts—potential cross-talk with IGF system. Growth Factors. 26(2):61-73.
[3] Alterio J, et al. (1990) Acidic and basic fibroblast growth factor mRNAs are expressed by skeletal muscle satellite cells. Biochem Biophys Res Commun. 166(3):1205-1212.
[4] Anderson J E, et al. (1991) Distinctive patterns of basic fibroblast growth factor (bFGF) distribution in degenerating and regenerating areas of dystrophic (mdx) striated muscles. Dev Biol. 147(1):96-109.
[5] Aracil A, et al. (2004) Proceedings of Neuropeptides 2004, the XIV European Neuropeptides Club meeting. Neuropeptides. 38 (6): 369-371.
[6] Arnold H H, et al. (1998) more complexity to the network of myogenic regulators. Curr Opin Genet Dev. 8(5):539-44.
[7] Arsic N, et al. (2004) Vascular endothelial growth factor stimulates skeletal muscle regeneration in vivo. Mol Ther. 10(5):844-854.
[8] Bandi E, et al. (2008) Neural agrin controls maturation of the excitation-contraction coupling mechanism in human myotubes developing in vitro. Am J Physiol Cell Physiol. 294(1):C66-73.
[9] Biesecker G, et al. (1990) The complement SC5b.9 complex mediates cell adhesion through a vitronectin receptor. J Immunol. 145(1):209-214.
[10] Bordet T., et al. (2001) Protective effects of cardiotrophin-1 adenoviral gene transfer on neuromuscular degeneration in transgenic ALS mice. Hum Mol Genet. 10(18): 1925-1933.
[11] Bottenstein J E, et al. (1988) CNS neuronal cell line-derived factors regulate gliogenesis in neonatal rat brain cultures. J Neurosci Res. 20(3):291-303.
[12] Bottenstein J E, et al. (1998) Advances in vertebrate cell culture methods. Science. 239(4841 Pt 2):G42, G48.
[13] Bottenstein J E, et al. (1981) Proliferation of glioma cells in serum-free defined medium. Cancer Treat Rep. 65 Suppl 2:67-70.
[14] Brand-Saberi B, et al. (2005) Genetic and epigenetic control of skeletal muscle development. Ann Anat. 187 (3):199-207.
[15] Bren-Mattison Y, et al. (2002) Sonic hedgehog inhibits the terminal differentiation of limb myoblasts committed to the slow muscle lineage. Dev Biol. 242(2):130-148.
[16] Brewer G J, et al. (2008) NbActiv4 medium improvement to Neurobasal/B27 increases neuron synapse densities and network spike rates on multielectrode arrays. J Neurosci Methods. 170(2):181-187.
[17] Brewer G J, et al. (1993) Optimized survival of hippocampal neurons in B27-supplemented Neurobasal, a new serum-free medium combination. J Neurosci Res. 35(5):567-576.
[18] Cannon J G, et al. (1998) Intrinsic and extrinsic factors in muscle aging Ann NY Acad Sci. 854:72-77.
[19] Caratsch C G, et al. (1994) Interferon-alpha, beta and tumor necrosis factor-alpha enhance the frequency of miniature end-plate potentials at rat neuromuscular junction. Neurosci Lett. 166(1):97-100.
[20] Carrasco Dl, et al. (2003) Neurotrophin 4/5 is required for the normal development of the slow muscle fiber phenotype in the rat soleus. J Exp Bio. 206(Pt 13):2191-2200.
[21] Chen J, et al. (2004) Role of exogenous and endogenous trophic factors in the regulation of extraocular muscle strength during development. Invest Ophthalmol Vis Sci. 45(10):3538-3545.
[22] Chen X, et al. (2005) Dedifferentiation of adult human myoblasts induced by ciliary neurotrophic factor in vitro. Mol Biol Cell. 16(7):3140-3151.
[23] Chen X P, et al. (2003) [Exogenous rhCNTF inhibits myoblast differentiation of skeletal muscle of adult human in vitro]. Sheng Li Xue Bao. 55(4):464-468.

[24] Choi-Lundberg D L, et al. (1995) Ontogeny and distribution of glial cell line-derived neurotrophic factor (GDNF) mRNA in rat. Brain Res Dev Brain Res. 85(1): 80-88.

[25] Chow I, et al. (1985) Release of acetylcholine from embryonic neurons upon contact with muscle cell. J Neurosci. 5(4):1076-82.

[26] Ciegg C H, et al. (1987) Growth factor control of skeletal muscle differentiation: commitment to terminal differentiation occurs in G1 phase and is repressed by fibroblast growth factor. J Cell Biol. 105(2):949-956.

[27] Colomar A, et al. (2004) Glial modulation of synaptic transmission at the neuromuscular junction. Glia. 47(3): 284-9.

[28] Cossu G, et al. (1996) How is myogenesis initiated in the embryo? Trends Genet. 12(6):218-223.

[29] Currie P D, et al. (1996) Induction of a specific muscle cell type by a hedgehog-like protein in zebrafish. Nature. 382(6590):452-455.

[30] Daniels M P, et al. (2000) Rodent nerve-muscle cell culture system for studies of neuromuscular junction development: refinements and applications. Microsc Res Tech. 49(1):26-37.

[31] Daniels M P, (1997) Intercellular communication that mediates formation of the neuromuscular junction. Mol Neurobiol. 14(3):143-170.

[32] Das M, et al. (2008) Temporal neurotransmitter conditioning restores the functional activity of adult spinal cord neurons in long-term culture. Exp Neurol. 209(1): 171-180.

[33] Das M, et al. (2005) Adult rat spinal cord culture on an organosilane surface in a novel serum-free medium. In Vitro Cell Dev Bioi Anim. 41(10):343-348.

[34] Das M, et al. (2003) Electrophysiological and morphological characterization of rat embryonic motoneurons in a defined system. Biotechnol Prog. 19(6):1756-1761.

[35] Das M, et al. (2004) Long-term culture of embryonic rat cardiomyocytes on an organosilane surface in a serum-free medium. Biomaterials. 25(25):5643-5647.

[36] Das M, et al. (2007) Auto-catalytic ceria nanoparticles offer neuroprotection to adult rat spinal cord neurons. Biomaterials. 28(10): 1918-1925.

[37] Das M, et al. (2009) Skeletal muscle tissue engineering: an improved model promoting long term survival of myotubes, structural development of e-c coupling apparatus and neonatal myosin heavy chain (MHC) expression. Biomaterials. 30:5392-402.

[38] Das M, et al. (2007) Embryonic motoneuron-skeletal muscle co-culture in a defined system. Neuroscience. 146(2):481-488.

[39] Das M, et al. (2007) Differentiation of skeletal muscle and integration of myotubes with silicon microstructures using serum-free medium and a synthetic silane substrate. Nat Protoc. 2(7): 1795-1801.

[40] Das M, et al. (2006) A defined system to allow skeletal muscle differentiation and subsequent integration with silicon microstructures. Biomaterials. 27(24):437 4-4380.

[41] Dell'Era P, et al. (2003) Fibroblast growth factor receptor 1 is essential for in vitro cardiomyocyte development. Circ Res. 93(5):414-420.

[42] Dolcet X, et al. (2001) Cytokines promote motoneuron survival through the Janus kinase-dependent activation of the phosphatidylinositol 3-kinase pathway. Mol Cell Neurosci. 18(6):619-631.

[43] Dusterhoft S, et al. (1999) Evidence that acidic fibroblast growth factor promotes maturation of rat satellite-cell-derived myotubes in vitro. Differentiation. 65(3): 161-169.

[44] Eisenberg T, et al. (2009) Induction of autophagy by spermidine promotes longevity. Nat Cell Biol. 11(11): 1305-14.

[45] Elia D, et al. (2007) Sonic hedgehog promotes proliferation and differentiation of adult muscle cells: Involvement of MAPK/ERK and P13K/Akt pathways. Biochim Biophys Acta. 1773(9):1438-1446.

[46] English A W., et al. (2003) Cytokines, growth factors and sprouting at the neuromuscular junction. J Neurocytol. 32(5):943-60.

[47] Fan C M, et al. (1994) Patterning of mammalian somites by surface ectoderm and notochord: evidence for sclerotome induction by a hedgehog homolog. Cell. 79(7):1175-1186.

[48] Foster R F, et al. (1987) A laminin substrate promotes myogenesis in rat skeletal muscle cultures: analysis of replication and development using antidesmin and anti-BrdUrd monoclonal antibodies. Dev Bio. 122(1):11-20.

[49] Fu X, et al. (1995) Acidic fibroblast growth factor reduces rat skeletal muscle damage caused by ischemia and reperfusion. Chin Med J (Engl). 108(3):209-214.

[50] Germani A, et al. (2003) Vascular endothelial growth factor modulates skeletal myoblast function. Am J Pathol. 163(4):1417-1428.

[51] Gold M R, et al. (1982) The effects of vasoactive intestinal peptide on neuromuscular transmission in the frog. J Physiol. 327:325-335.

[52] Golden J P, et al. (1999) Expression of neurturin, GDNF, and GDNF family-receptor mRNA in the developing and mature mouse. Exp Neural. 158(2):504-528.

[53] Gonzalez A M, et al. (1990) Distribution of basic fibroblast growth factor in the 18-day rat fetus: localization in the basement membranes of diverse tissues. J Cell Biol. 110(3):753-765.

[54] Gozes I, et al. (2004) NAP mechanisms of neuroprotection. J Mol Neurosci. 24(1):67-72.

[55] Gullberg D, et al. (1995) Analysis of fibronectin and vitronectin receptors on human fetal skeletal muscle cells upon differentiation. Exp Cell Res. 220(1):112-123.

[56] Hall B K, et al. (2000) All for one and one for all: condensations and the initiation of skeletal development. Bioessays. 22(2): 138-147.

[57] Hantai D, et al. (1991) Developmental appearance of thrombospondin in neonatal mouse skeletal muscle. Eur J Cell Biol. 55(2):286-294.

[58] Heinrich G, et al. (2003) A novel BDNF gene promoter directs expression to skeletal muscle. BMC Neurosci. 4:11.

[59] Henderson C E, et al. (1994) GDNF: a potent survival factor for motoneurons present in peripheral nerve and muscle. Science. 266(5187):1062-1064.

[60] Husmann I, et al. (1996) Growth factors in skeletal muscle regeneration. Cytokine Growth Factor Rev. 7(3): 249-258.

[61] Jaworska-Wilczynska M, et al. (2002) Three lipoprotein receptors and cholesterol in inclusion-body myositis muscle. Neurology. 58(3):438-445.

[62] Jin P, et al. (1991) Recombinant platelet-derived growth factor-88 stimulates growth and inhibits differentiation of rat L6 myoblasts. J Biol Chem. 266(2):1245-1249.

[63] Koleva M, et al. (2005) Pleiotropic effects of sonic hedgehog on muscle satellite cells. Cell Mol Life Sci. 62(16): 1863-1870.

[64] Kudla A J, et al. (1995) A requirement for fibroblast growth factor in regulation of skeletal muscle growth and differentiation cannot be replaced by activation of platelet-derived growth factor signaling pathways. Mol Cell Biol. 15(6):3238-3246.

[65] Kuhl U, et al. (1986) Role of laminin and fibronectin in selecting myogenic versus fibrogenic cells from skeletal muscle cells in vitro. Dev Biol. 117(2):628-635.

[66] Kurek J B, et al. (1996) Leukemia inhibitory factor and interleukin-6 are produced by diseased and regenerating skeletal muscle. Muscle Nerve. 19(10):1291-1301.

[67] Langen R C, et al. (2003) Enhanced myogenic differentiation by extracellular matrix is regulated at the early stages of myogenesis. In Vitro Cell Dev Biol Anim. 39(3-4): 163-169.

[68] Lee E W., et al. (2003) Neuropeptide Y induces ischemic angiogenesis and restores function of ischemic skeletal muscles. J Clin Invest. 111(12): 1853-1862.

[69] Lesbordes J C, et al. (2002) In vivo electrotransfer of the cardiotrophin-1 gene into skeletal muscle slows down progression of motor neuron degeneration in pmn mice. Hum Mol Genet. 11(14):1615-1625.

[70] Lescaudron L, et al. (1999) Blood borne macrophages are essential for the triggering of muscle regeneration following muscle transplant. Neuromuscul Disord. 9(2):72-80.

[71] Li M X, et al. (2001) Opposing actions of protein kinase A and C mediate Hebbian synaptic plasticity. Nat Neurosci. 4(9):871-872.

[72] Lin L F, et al. (1993) GDNF: a glial cell line-derived neurotrophic factor for midbrain dopaminergic neurons. Science. 260(5111):1130-1132.

[73] Lyles J M, et al. (1992) Matrigel enhances myotube development in a serum-free defined medium. Int J Dev Neurosci. 10(1):59-73.

[74] Malm C, et al. (2004) Leukocytes, cytokines, growth factors and hormones in human skeletal muscle and blood after uphill or downhill running J Physiol. 556(Pt 3):983-1000.

[75] Marques M J, et al. (1997) Ciliary neurotrophic factor stimulates in vivo myotube formation in mice. Neurosci Lett. 234(1):43-46.

[76] Martinou J C, et al. (1992) Cholinergic differentiation factor (CDF/LIF) promotes survival of isolated rat embryonic motoneurons in vitro. Neuron. 8(4):737-744.

[77] Mayes L, et al. (2007) Pbx homeodomain proteins direct Myod activity to promote fast-muscle differentiation. Development. 134 (18):3371-3382.

[78] Megeney L A, et al. (1996) bFGF and LIF signaling activates STAT3 in proliferating myoblasts. Dev Genet. 19(2):139-145.

[79] Miller S C, et al. (1998) Tumor necrosis factor inhibits human myogenesis in vitro. Mol Cell Biol. 8(6):2295-2301.

[80] Mitsumoto H, et al. (2001) Effects of cardiotrophin.1 (CT-1) in a mouse motor neuron disease. Muscle Nerve. 24(6):769-777.

[81] Moore J W, et al. (1991) The mRNAs encoding acidic FGF, basic FGF and FGF receptor are coordinately down-regulated during myogenic differentiation. Development. 111(3):741-748.

[82] Morrow N G, et al. (1990) Increased expression of fibroblast growth factors in a rabbit skeletal muscle model of exercise conditioning. J Clin Invest. 85(6):1816-1820.

[83] Motamed K, et al. (2003) Fibroblast growth factor receptor-1 mediates the inhibition of endothelial cell proliferation and the promotion of skeletal myoblast differentiation by SPARC: a role for protein kinase A. J Cell Biochem. 90(2):408-423.

[84] Mousavi K, et al. (2004) BDNF rescues myosin heavy chain 118 muscle fibers after neonatal nerve injury. Am J Physiol Cell Physicl. 287(1):C22-29.

[85] Munsterberg A E, et al. (1995) Combinatorial signaling by Sonic hedgehog and Wnt family members induces myogenic bHLH gene expression in the somite. Genes Dev. 9(23):2911-2922.

[86] Nelson C E, et al. (1996) Analysis of Hox gene expression in the chick limb bud. Development. 122(5): 1449-1466.

[87] Nelson P G (1975) Nerve and muscle cells in culture. Physiol Rev. 55(1):1-61.

[88] Nishikawa J, et al. (2005) Increase of Cardiotrophin-1 immunoreactivity in regenerating and overloaded but not denervated muscles of rats. Neuropathology. 25(1): 54-65.

[89] Norris W, et al. (2000) Slow muscle induction by Hedgehog signalling in vitro. J Cell Sci. 113 (Pt 15):2695-2703.

[90] Oliver L, et al. (1992) Acidic fibroblast growth factor (aFGF) in developing normal and dystrophic (mdx) mouse muscles. Distribution in degenerating and regenerating mdx myofibres. Growth Factors. 7(2):97-106.

[91] Oakley R A, et al. (1997) Neurotrophin-3 promotes the differentiation of muscle spindle afferents in the absence of peripheral targets. J Neurosci. 17(11):4262-4274.

[92] Olson E N., et al. (1992) Interplay between proliferation and differentiation within the myogenic lineage. Dev Biol. 154(2):261-72.

[93] Olwin B B, et al. (1992) Repression of myogenic differentiation by aFGF, bFGF, and K.FGF is dependent on cellular heparan sulfate. J Cell Biol. 118(3):631-639.

[94] Oppenheim R W, et al. (2001) Cardiotrophin-1, a muscle-derived cytokine, is required for the survival of subpopulations of developing motoneurons. J Neurosci. 21(4):1283-1291.

[95] Pagan S M, et al. (1996) Surgical removal of limb bud Sonic hedgehog results in posterior skeletal defects. Dev Biol. 180(1):35-40.

[96] Peroulakis M E, et al. (2000) Forger NG: Ciliary neurotrophic factor increases muscle fiber number in the developing levator ani muscle of female rats. Neurosci Lett. 296(2-3):73-76.

[97] Quinn L S, et al. (1990) Paracrine control of myoblast proliferation and differentiation by fibroblasts. Dev Biol. 140(1):8-19.

[98] Ravenscroft M S, et al. (1998) Developmental Neurobiology Implications from Fabrication and Analysis of Hippocampal Neuronal Networks on Patterned Silane-Modified Surfaces. J Am Chem Soc. 120(47):12169-12177.

[99] Robertson T A, et al. (2000) Comparison of astrocytic and myocytic metabolic dysregulation in apolipoprotein E deficient and human apolipoprotein E transgenic mice. Neuroscience. 98(2):353-359.

[100] Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497(1):77-88.

[101] Sandi E, et al. (2008) Neural agrin controls maturation of the excitation-contraction coupling mechanism in human myotubes developing in vitro. Am J Physiol, Cell Physiol. 294(1):C66-73.

[102] Sanes J R, et al. (1997) Genetic analysis of postsynaptic differentiation at the vertebrate neuromuscular junction. Curr Opin Neurobiol. 7(1):93-100.

[103] Sheng Z, et al. (1996) Cardiotrophin-1 displays early expression in the murine heart tube and promotes cardiac myocyte survival. Development. 122(2):419-428.

[104] Simon M, et al. (2003) Effect of NT-4 and BDNF delivery to damaged sciatic nerves on phenotypic recovery of fast and slow muscles fibres. Eur J Neurosci. 18(9):2460-2466.

[105] Smith J, et al. (1994) The effects of fibroblast growth factors in long-term primary culture of dystrophic (mdx) mouse muscle myoblasts. Exp Cell Res. 210(1):86-93.

[106] Song W K, et al. (1992) H36-alpha 7 is a novel integrin alpha chain that is developmentally regulated during skeletal myogenesis. J Cell Biol. 117(3):643-657.

[107] Stenger D A, et al. (1992) Coplanar molecular assemblies of aminoalkylsilane and perfluorinated alkylsilane—characterization and geometric definition of mammalian-cell adhesion and growth. J Am Chem Soc. 114(22):8435-42.

[108] Sun L, et al. (2007) JAK1-STAT1.-STAT3, a key pathway promoting proliferation and preventing premature differentiation of myoblasts. J Cell Biol. 179(1): 129-138.

[109] Swasdison S, et al. (1992) Formation of highly organized skeletal muscle fibers in vitro. Comparison with muscle development in vivo. J Cell Sci. 102 (Pt 3):643-652.

[110] Torgan C E, et al. (2006) Calcineurin localization in skeletal muscle offers insights into potential new targets. J Histochem Cytochem. 54(1): 119-128.

[111] Torgan C E, et al. (2001) Regulation of myosin heavy chain expression during rat skeletal muscle development in vitro. Mol Bioi Cell. 12(5): 1499-1508.

[112] Vakakis N, et al. (1995) In vitro myoblast to myotube transformations in the presence of leukemia inhibitory factor. Neurochem Int. 27(4-5):329-335.

[113] Vogel Z, et al. (1976) Ultrastructure of acetylcholine receptor clusters on cultured muscle fibers. J Cell Biol. 69(2):501-507.

[114] Wang P, et al. (2005) Defective neuromuscular synapses in mice lacking amyloid precursor protein (APP) and APP-Like protein 2. J Neurosci. 25(5): 1219-1225.

[115] Wang X, et al. (2008) Effects of interleukin-6, leukemia inhibitory factor, and ciliary neurotrophic factor on the proliferation and differentiation of adult human myoblasts. Cell Mol Neurobiol. 28(1): 113-124.

[116] Witzemann V., (2006) Development of the neuromuscular junction. Cell Tissue Res. 326(2):263-71.

[117] Yablonka-Reuveni Z, et al. (1995) Development and postnatal regulation of adult myoblasts. Microsc Res Tech. 30(5):366-380.

[118] Yang L, et al. (2007) Increased asynchronous release and aberrant calcium channel activation in amyloid precursor protein deficient neuromuscular synapses. Neuroscience. 149(4):768-778.

[119] Yang L X, et al. (2004) Glia cell line-derived neurotrophic factor regulates the distribution of acetylcholine receptors in mouse primary skeletal muscle cells. Neuroscience. 128(3):497-509.

[120] Zorzano A, et al. (2003) Intracellular signals involved in the effects of insulin-like growth factors and neuregulins on myofibre formation. Cell Signal. 15(2):141-149.

The invention claimed is:

1. A co-culture for forming at least one synthetic mammalian neuromuscular junction, comprising: fetal mammalian skeletal muscle cells adhered to an artificial surface and overlayered with fetal mammalian spinal motoneurons in a serum-free medium, wherein the serum-free medium comprises a mixture of the components of Table 3 at the concentrations listed in Table 3, the components of Table 4 at the concentrations listed in Table 4, the components of Table 5 at the concentrations listed in Table 5, creatine, estrogen, and cholesterol.

2. The co-culture of claim 1, wherein one or more of the fetal mammalian spinal motoneurons is functionally linked to one or more of the fetal mammalian skeletal muscle cells.

3. The co-culture of claim 1, wherein the artificial surface comprises a silicon based monolayer substrate deposited thereon.

4. The co-culture of claim 3, wherein the silicon based monolayer substrate is deposited in a predetermined pattern.

5. The co-culture of claim 3, wherein the silicon based monolayer substrate comprises trimethoxysilylpropyl diethylenetriamine (DETA).

6. The co-culture of claim 1, wherein the fetal mammalian skeletal muscle cells have a density of about from 700 to about 1000 cells/mm$^2$.

7. The co-culture of claim 1, wherein the fetal mammalian spinal motoneurons have a density of about 100 cells/mm$^2$.

* * * * *